United States Patent
Grewal et al.

(10) Patent No.: US 10,605,781 B2
(45) Date of Patent: Mar. 31, 2020

(54) METHODS FOR MEASURING OUT-OF-PLANE WRINKLES IN COMPOSITE LAMINATES

(71) Applicant: The Boeing Company, Chicago, IL (US)

(72) Inventors: Navpreet S. Grewal, Redmond, WA (US); Gary E. Georgeson, Tacoma, WA (US); Jill P. Bingham, Seattle, WA (US); John D. Morris, Seattle, WA (US); Sabyasachi Basu, Redmond, WA (US)

(73) Assignee: The Boeing Company, Chicago, IL (US)

( * ) Notice: Subject to any disclaimer, the term of this patent is extended or adjusted under 35 U.S.C. 154(b) by 151 days.

(21) Appl. No.: 15/917,321

(22) Filed: Mar. 9, 2018

(65) Prior Publication Data
US 2019/0277808 A1 Sep. 12, 2019

(51) Int. Cl.
*G01N 29/06* (2006.01)
*G01N 29/04* (2006.01)
(Continued)

(52) U.S. Cl.
CPC ....... *G01N 29/0672* (2013.01); *G01N 29/041* (2013.01); *G01N 29/043* (2013.01);
(Continued)

(58) Field of Classification Search
CPC ............ G01N 29/0672; G01N 29/041; G01N 29/223; G01N 29/043; G01N 29/0645;
(Continued)

(56) References Cited

U.S. PATENT DOCUMENTS 5,554,808 A 9/1996 Chiao
8,499,632 B1 8/2013 Ihn et al.
(Continued)

FOREIGN PATENT DOCUMENTS

EP 1952137 8/2008
WO 2007058926 5/2007

OTHER PUBLICATIONS

European Patent Office, "Extended European Search Report," issued in connection with European Patent Application No. 19150053.7, dated Aug. 8, 2019, 8 pages.
(Continued)

*Primary Examiner* — Suman K Nath
(74) *Attorney, Agent, or Firm* — Hanley, Flight & Zimmerman, LLC

(57) ABSTRACT

Methods for measuring out-of-plane wrinkles in composite laminates are described. An example method includes scanning a first side of a composite laminate with an ultrasonic transducer. The method further includes locating an out-of-plane wrinkle of the composite laminate on a B-scan ultrasound image generated in response to the scanning of the first side of the composite laminate. The method further includes associating a first marker with the B-scan ultrasound image, the first marker determined based on a location of a crest of the out-of-plane wrinkle on the B-scan ultrasound image. The method further includes associating a second marker with the B-scan ultrasound image, the second marker determined based on a location of a trough focal point of the out-of-plane wrinkle on the B-scan ultrasound image. The method further includes determining an amplitude of the out-of-plane wrinkle based on a distance between the first marker and the second marker.

18 Claims, 15 Drawing Sheets

(51) Int. Cl.
  *G01N 29/22* (2006.01)
  *G01N 29/44* (2006.01)
  *G01N 29/265* (2006.01)

(52) U.S. Cl.
  CPC ..... *G01N 29/0609* (2013.01); *G01N 29/0645* (2013.01); *G01N 29/223* (2013.01); *G01N 29/265* (2013.01); *G01N 29/4454* (2013.01); *G01N 2291/0231* (2013.01); *G01N 2291/044* (2013.01); *G01N 2291/2694* (2013.01)

(58) Field of Classification Search
  CPC ................. G01N 29/346; G01N 29/46; G01N 2291/0231; G01N 2291/2694
  USPC ................................................... 73/584, 602
  See application file for complete search history.

(56) References Cited

U.S. PATENT DOCUMENTS

| | | |
|---|---|---|
| 2017/0199160 A1 | 7/2017 | Dehghan Niri et al. |
| 2017/0299381 A1* | 10/2017 | Bingham ............... G01B 17/00 |
| 2018/0120268 A1* | 5/2018 | Georgeson ............ G01N 29/07 |

OTHER PUBLICATIONS

Smith et al., "Ultrasonic Analytic-Signal Responses From Polymer-Matrix Composite Laminates," IEEE Transactions on Ultrasonics, Ferroelectrics, and Frequency Control, vol. 65, No. 2, Feb. 2018, 13 pages.

\* cited by examiner

METHODS FOR MEASURING OUT-OF-PLANE WRINKLES IN COMPOSITE LAMINATES

FIELD OF THE DISCLOSURE

This disclosure relates generally to methods for measuring wrinkles and, more particularly, to methods for measuring out-of-plane wrinkles in composite laminates.

BACKGROUND

Composite laminates are commonly implemented in aircraft and other structures. For example, an aircraft may include numerous composite laminates implemented as stringers for a wing assembly of the aircraft. A composite laminate may contain one or more out-of-plane wrinkle(s) (e.g., one or more internal material wrinkle(s) formed and/or extending along a thickness dimension of the composite laminate) that are not visible and/or not exposed on any external surface of the composite laminate.

The height of an out-of-plane wrinkle may be used to predict the performance of the out-of-plane wrinkle and/or the performance of the composite laminate in which the out-of-plane wrinkle is present. With the out-of-plane wrinkle being located internally and/or within the composite laminate, the process of determining the height of the out-of-plane wrinkle conventionally requires cutting the composite laminate parallel to its thickness dimension. In response to cutting the composite laminate in this manner, the out-of-plane wrinkle may become visible and/or exposed on a newly-formed external surface of the composite laminate, thereby enabling an optical measurement of the out-of-plane wrinkle. Conventional techniques for measuring an out-of-plane wrinkle in a composite laminate are accordingly disadvantageous in that such techniques result in the destruction and/or physical alteration of the composite laminate.

SUMMARY

Methods for measuring out-of-plane wrinkles in composite laminates are disclosed. In some examples, a method is disclosed. In some disclosed examples, the method comprises scanning a first side of a composite laminate with an ultrasonic transducer. In some disclosed examples, the method comprises locating an out-of-plane wrinkle of the composite laminate on a B-scan ultrasound image generated in response to the scanning of the first side of the composite laminate. In some disclosed examples, the method comprises associating a first marker with the B-scan ultrasound image. In some disclosed examples, the first marker is determined based on a location of a crest of the out-of-plane wrinkle on the B-scan ultrasound image. In some disclosed examples, the method comprises associating a second marker with the B-scan ultrasound image. In some disclosed examples, the second marker is determined based on a location of a trough focal point of the out-of-plane wrinkle on the B-scan ultrasound image. In some disclosed examples, the method comprises determining an amplitude of the out-of-plane wrinkle based on a distance between the first marker and the second marker.

In some examples, a method is disclosed. In some disclosed examples, the method comprises scanning a first side of a composite laminate with a first ultrasonic transducer. In some disclosed examples, the method comprises locating an out-of-plane wrinkle of the composite laminate on a first B-scan ultrasound image generated in response to the scanning of the first side of the composite laminate. In some disclosed examples, the method comprises associating a first marker with the first B-scan ultrasound image. In some disclosed examples, the first marker is determined based on a location of a crest of the out-of-plane wrinkle on the first B-scan ultrasound image. In some disclosed examples, the method comprises associating a second marker with the first B-scan ultrasound image. In some disclosed examples, the second marker is determined based on a location of a trough focal point of the out-of-plane wrinkle on the first B-scan ultrasound image. In some disclosed examples, the method comprises determining a first amplitude of the out-of-plane wrinkle based on a distance between the first marker and the second marker. In some disclosed examples, the method comprises scanning a second side of the composite laminate opposite the first side with a second ultrasonic transducer. In some disclosed examples, the method comprises locating the out-of-plane wrinkle of the composite laminate on a second B-scan ultrasound image generated in response to the scanning of the second side of the composite laminate. In some disclosed examples, the method comprises associating a third marker with the second B-scan ultrasound image. In some disclosed examples, the third marker is determined based on a location of a trough of the out-of-plane wrinkle on the second B-scan ultrasound image. In some disclosed examples, the method comprises associating a fourth marker with the second B-scan ultrasound image. In some disclosed examples, the fourth marker is determined based on a location of a crest focal point of the out-of-plane wrinkle on the second B-scan ultrasound image. In some disclosed examples, the method comprises determining a second amplitude of the out-of-plane wrinkle based on a distance between the third marker and the fourth marker.

Certain examples are shown in the above-identified figures and described in detail below. In describing these examples, like or identical reference numbers are used to identify the same or similar elements. The figures are not necessarily to scale and certain features and certain views of the figures may be shown exaggerated in scale or in schematic for clarity and/or conciseness.

DETAILED DESCRIPTION

As described above, conventional techniques for measuring an out-of-plane wrinkle in a composite laminate result in the destruction and/or physical alteration of the composite laminate. Unlike such conventional measurement techniques, the methods disclosed herein for measuring out-of-plane wrinkles in composite laminates are non-destructive and/or do not result in any physical alteration of a composite laminate that is subjected to such methods. The disclosed methods enable the height of an out-of-plane wrinkle in a composite laminate to advantageously be measured, calculated, and/or determined in a non-destructive manner. The disclosed non-destructive measurement techniques may be especially useful for qualifying and/or certifying that a composite laminate does not include any out-of-plane wrinkles exceeding a specified and/or threshold height.

Figure 1:
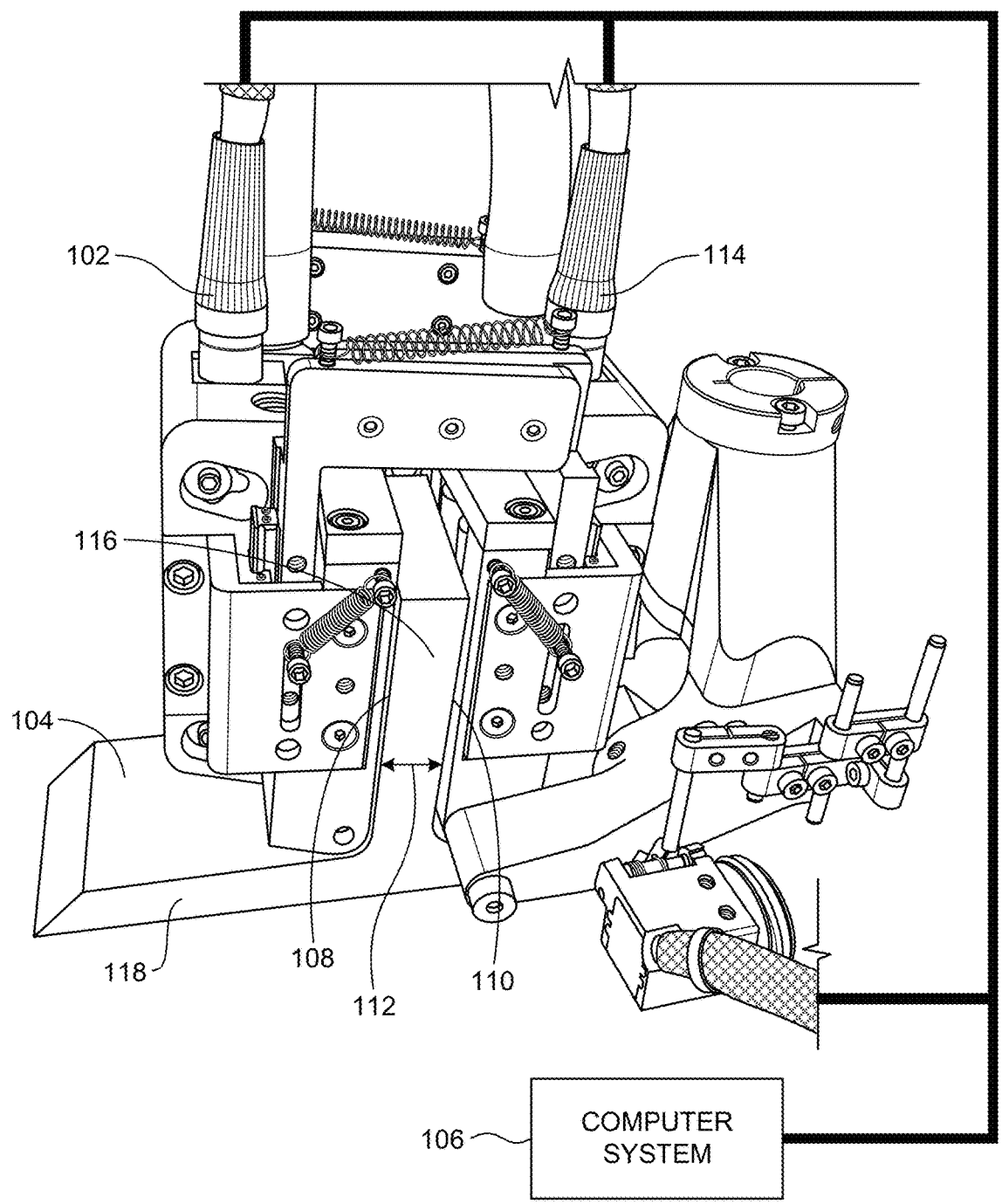
FIG. 1 is a schematic of an example ultrasonic transducer that may be implemented to scan an example composite laminate in accordance with the teachings of this disclosure.

FIG. 1 is a schematic of an example ultrasonic transducer 102 that may be implemented to scan an example composite laminate 104 in accordance with the teachings of this disclosure. In the illustrated example of FIG. 1, the ultrasonic transducer 102 is removably coupled to the composite laminate 104 and operatively coupled to (e.g., in electrical communication with) an example computer system 106. In other examples, the ultrasonic transducer 102 may be directed and/or targeted toward the composite laminate 104 without being removably coupled thereto. The ultrasonic transducer 102 of FIG. 1 is a five megahertz, one hundred twenty-eight element, 0.020 inch pitch, 0.250 width ultrasonic transducer. In other examples, the ultrasonic transducer 102 may operate at a different frequency, have a different number of elements, a different pitch, and/or a different width. For example, the ultrasonic transducer 102 may operate at a frequency greater than five megahertz (e.g., 7.5 megahertz) to increase the resolution of ultrasonic B-scan data obtained and/or acquired via the ultrasonic transducer 102.

In the illustrated example of FIG. 1, the composite laminate 104 is a stringer coupon (e.g., a segment of a complete stringer). In other examples, the composite laminate 104 may be a stringer (e.g., a complete stringer). In still other examples, the composite laminate 104 may be a composite laminate structure of any shape and/or type, including for example a composite laminate to be installed in and/or on an aircraft. The composite laminate 104 of FIG. 1 includes an example first side 108, an example second side 110 located opposite the first side 108, and an example thickness 112 extending between the first side 108 and the second side 110. The first side 108 and/or the second side 110 of the composite laminate 104 define(s) a first plane (e.g., a C-plane) associated with an ultrasonic scan of the composite laminate 104 to be obtained and/or acquired via the ultrasonic transducer 102 (e.g., ultrasonic C-scan data). The thickness 112 of the composite laminate 104 define(s) a second plane (e.g., a B-plane) positioned orthogonally to the first plane and associated with the ultrasonic scan of the composite laminate 104 to be obtained and/or acquired via the ultrasonic transducer 102 (e.g., ultrasonic B-scan data). The composite laminate 104 of FIG. 1 may include one or more out-of-plane wrinkle(s) located between the first side 108 and the second side 110 of the composite laminate 104 and extending in the direction of the second plane (e.g., the B-plane) along the thickness 112 of the composite laminate 104.

In the illustrated example of FIG. 1, the ultrasonic transducer 102 is directed and/or targeted toward the first side 108 of the composite laminate 104 such that the ultrasonic transducer 102 is closer and/or more proximate to the first side 108 of the composite laminate 104 than the second side 110 of the composite laminate 104. In other examples, the ultrasonic transducer 102 of FIG. 1 may instead be directed toward, and/or targeted toward the second side 110 of the composite laminate 104 such that the ultrasonic transducer 102 is closer and/or more proximate to the second side 110 of the composite laminate 104 than the first side 108 of the composite laminate 104. For example, the composite laminate 104 may be rotated approximately one hundred eighty degrees relative to the position shown in FIG. 1, such that the ultrasonic transducer 102 of FIG. 1 is directed and/or targeted toward the second side 110 of the composite laminate 104 rather than the first side 108 of the composite laminate 104. The ultrasonic transducer 102 of FIG. 1 may accordingly be implemented to scan the first side 108 or the second side 110 of the composite laminate 104.

In still other examples, a second example ultrasonic transducer 114 operatively coupled to the computer system 106 may additionally or alternatively be removably coupled to, directed toward, and/or targeted toward the second side 110 of the composite laminate 104. In some such other examples, the ultrasonic transducer 102 of FIG. 1 may be implemented to scan the first side 108 of the composite laminate 104, and the second ultrasonic transducer 114 may be implemented to scan the second side 110 of the composite laminate 104. In some examples, the second ultrasonic transducer 114 of FIG. 1 may have a configuration that matches that of the ultrasonic transducer 102 described above (e.g., a five megahertz, one hundred twenty-eight element, 0.020 inch pitch, 0.250 width ultrasonic transducer). In other examples, the second ultrasonic transducer 114 of FIG. 1 may have a configuration that differs from that of the ultrasonic transducer 102 described above.

The computer system 106 of FIG. 1 may be implemented as one or more ultrasound workstations(s), desktop computer(s), laptop computer(s), server(s), tablet(s), or any other type of computing device. The computer system 106 of FIG. 1 instructs, commands, and/or controls the ultrasonic transducer 102 and/or the second ultrasonic transducer 114 to scan the composite laminate 104. The computer system 106 of FIG. 1 also processes and/or analyzes ultrasonic data obtained and/or acquired via the ultrasonic transducer 102 and/or the second ultrasonic transducer 114 in connection with the scanning of the composite laminate 104. For example, the computer system 106 may generate ultrasonic B-scan images and ultrasonic C-scan images based respectively on ultrasonic B-scan data and ultrasonic C-scan data obtained and/or acquired via the ultrasonic transducer 102 and/or the second ultrasonic transducer 114, as is conventionally known in the art.

In some examples, the computer system 106 of FIG. 1 may include one or more processor(s), one or more storage device(s) or storage disk(s) (e.g., a hard drive, flash memory, etc.), one or more input device(s) (e.g., a mouse, a keyboard, the ultrasonic transducer 102, the second ultrasonic transducer 114, etc.), and/or one or more output device(s) (e.g., a display or monitor, speakers, a printer, etc.). In some examples, the computer system 106 may also include ultrasound data processing and/or analysis software conventionally known in the art. In some such examples, the ultrasound data processing and/or analysis software may be used to assist an end user in performing one or more operation(s) of the disclosed methods for measuring out-of-plane wrinkles of composite laminates. In other examples, the computer system 106 may additionally or alternatively include machine-readable instructions comprising one or more program(s) for execution by the computer system 106 for automatically performing one or more operation(s) of the disclosed methods for measuring out-of-plane wrinkles of composite laminates. In some such other examples, the machine-readable instructions may implement one or more computer vision and/or image processing techniques and/or algorithms to identify, determine, locate, and/or measure one or more feature(s) of one or more out-of-plane wrinkle(s) of a composite laminate based on ultrasonic B-scan data acquired and/or obtained from the ultrasonic transducer 102 and/or the second ultrasonic transducer 114 of FIG. 1.

In some examples, the computer system 106 of FIG. 1 may be used to calibrate the ultrasonic transducer 102 and/or the second ultrasonic transducer 114 of FIG. 1 relative to the thickness 112 of the composite laminate 104 of FIG. 1. Calibration may ensure that the ultrasonic transducer 102 and/or the second ultrasonic transducer 114 is/are able to obtain and/or acquire ultrasonic B-scan data corresponding to the entirety of the thickness 112 of the composite laminate 104. Calibration may further ensure that a material velocity for the ultrasonic transducer 102 and/or the second ultrasonic transducer 114 is correctly set. In some examples, a calibration process may include setting a screen range (e.g., a data range from a front side signal of the composite laminate 104 to a back side signal of the composite laminate 104) to cover approximately eighty percent of an un-zoomed screen, and/or to cover the entirety of the thickness 112 of the composite laminate 104. In some examples, setting the screen range may include implementing and/or adjusting a distance amplitude correction (DAC) setting or a time gain compensation (TGC) setting. The calibration process may further include ultrasonically scanning a step wedge of at least three different steps in relation to the thickness 112 of the composite laminate 104 (e.g., ¼T, ½T, and T, where T is the thickness 112 of the composite laminate 104). The calibration process may further include setting a precision associated with ultrasonic B-scan cursor readings to three or four decimal places.

Although the description of FIG. 1 provided above is directed to scanning a first example portion 116 of the composite laminate 104, other portions of the composite laminate 104 may be scanned in a similar manner. For example, a second example portion 118 of the composite laminate 104 may be scanned via ultrasonic the transducer 102 and/or the second ultrasonic transducer 114 of FIG. 1 in a manner that is substantially identical to that described above in relation to the first portion 116 of the composite laminate 104. The disclosed methods for measuring out-of-plane wrinkles may accordingly be applied to any type and/or shape of composite laminate, including any portions thereof.

Figure 2:
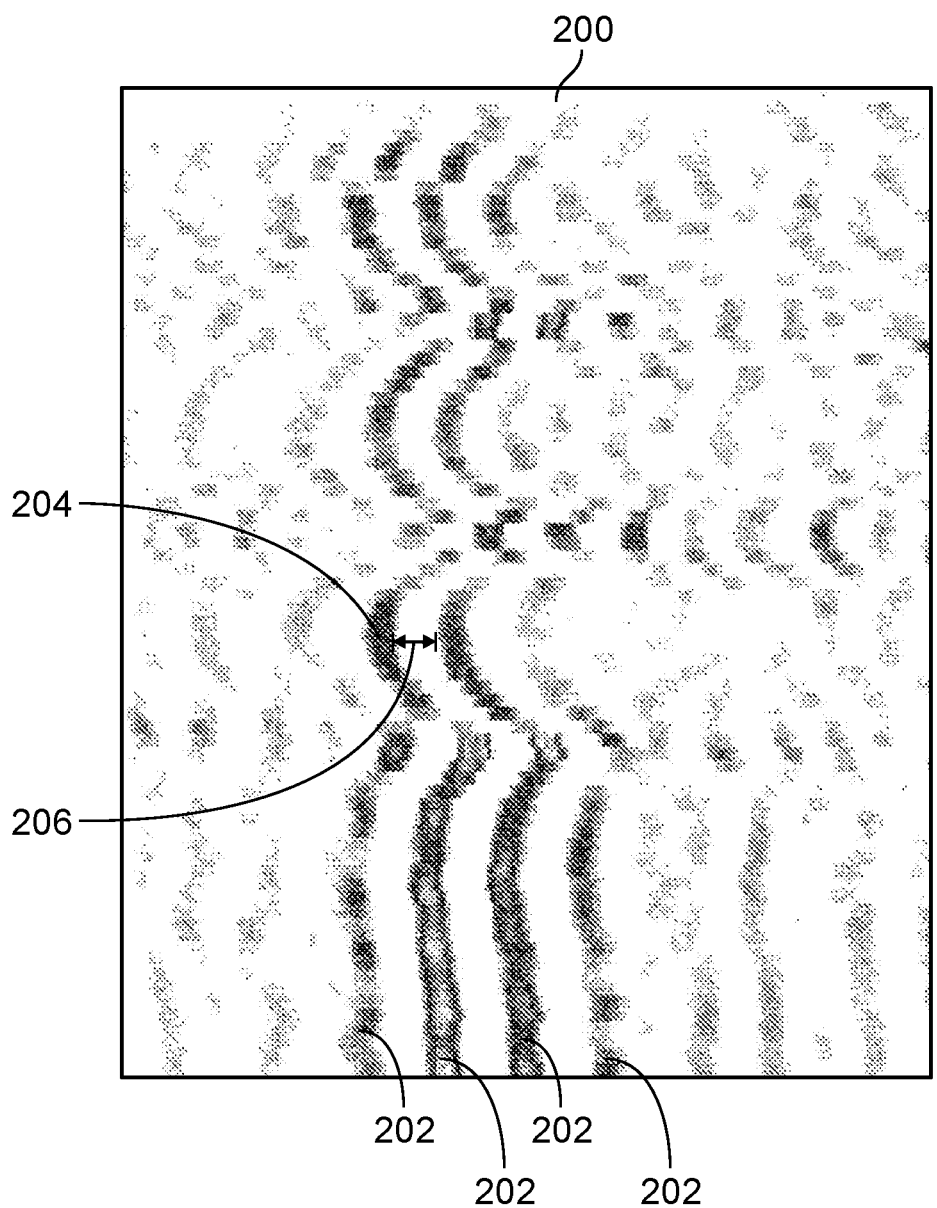
FIG. 2 is an example B-scan ultrasound image generated in response to ultrasonically scanning a composite laminate.

FIG. 2 is an example B-scan ultrasound image 200 generated in response to ultrasonically scanning a composite laminate. For example, the B-scan ultrasound image 200 of FIG. 2 may be generated and displayed via the computer system 106 of FIG. 1 based on ultrasonic B-scan data obtained and/or acquired via the ultrasonic transducer 102 or the second ultrasonic transducer 114 of FIG. 1. In some examples, the B-scan ultrasound image 200 of FIG. 2 may correspond to ultrasonic B-scan data associated with the ultrasonic transducer 102 scanning the first side 108 of the composite laminate 104 of FIG. 1. In other examples, the B-scan ultrasound image 200 of FIG. 2 may instead correspond to ultrasonic B-scan data associated with the ultrasonic transducer 102 or the second ultrasonic transducer 114 scanning the second side 110 of the composite laminate 104 of FIG. 1.

In the illustrated example of FIG. 2, the B-scan ultrasound image 200 includes a plurality of example out-of-plane wrinkles 202. Respective ones of the out-of-plane wrinkles 202 are indicated graphically and/or visually in the B-scan ultrasound image 200 by a data pulse (e.g., a darkened portion of the B-scan ultrasound image 200) followed by an empty and/or free space (e.g., a white portion of the B-scan ultrasound image 200. In some examples, portions of the respective ones of the out-of-plane wrinkles 202 of the B-scan ultrasound image 200 have a wave-like and/or sinusoidal shape. In some such examples, a height and/or amplitude associated with the wave-like and/or sinusoidal portions of the out-of-plane wrinkles 202 may vary from one of the out-of-plane wrinkles 202 to the next. For example, an example first one 204 of the out-of-plane wrinkles 202 of FIG. 2 may have an example amplitude 206 that is greater than the amplitudes associated with other ones of the out-of-plane wrinkles 202. In such an example, the first one 204 of the out-of-plane wrinkles 202 of FIG. 2 may be characterized as the most severe and/or the worst of the out-of-plane wrinkles 202 included in the B-scan ultrasound image 200 of FIG. 2. In some examples, the most severe and/or the worst of the out-of-plane wrinkles 202 (e.g., the first one 204 of the out-of-plane wrinkles 202) may be chosen or selected for analysis in connection with the disclosed methods for measuring out-of-plane wrinkles of composite laminates. In other examples, several of the out-of-plane wrinkles 202 (which may or may not include the most severe and/or the worst of the out-of-plane wrinkles 202) may be chosen or selected for analysis in connection with the disclosed methods for measuring out-of-plane wrinkles of composite laminates.

Figure 3:
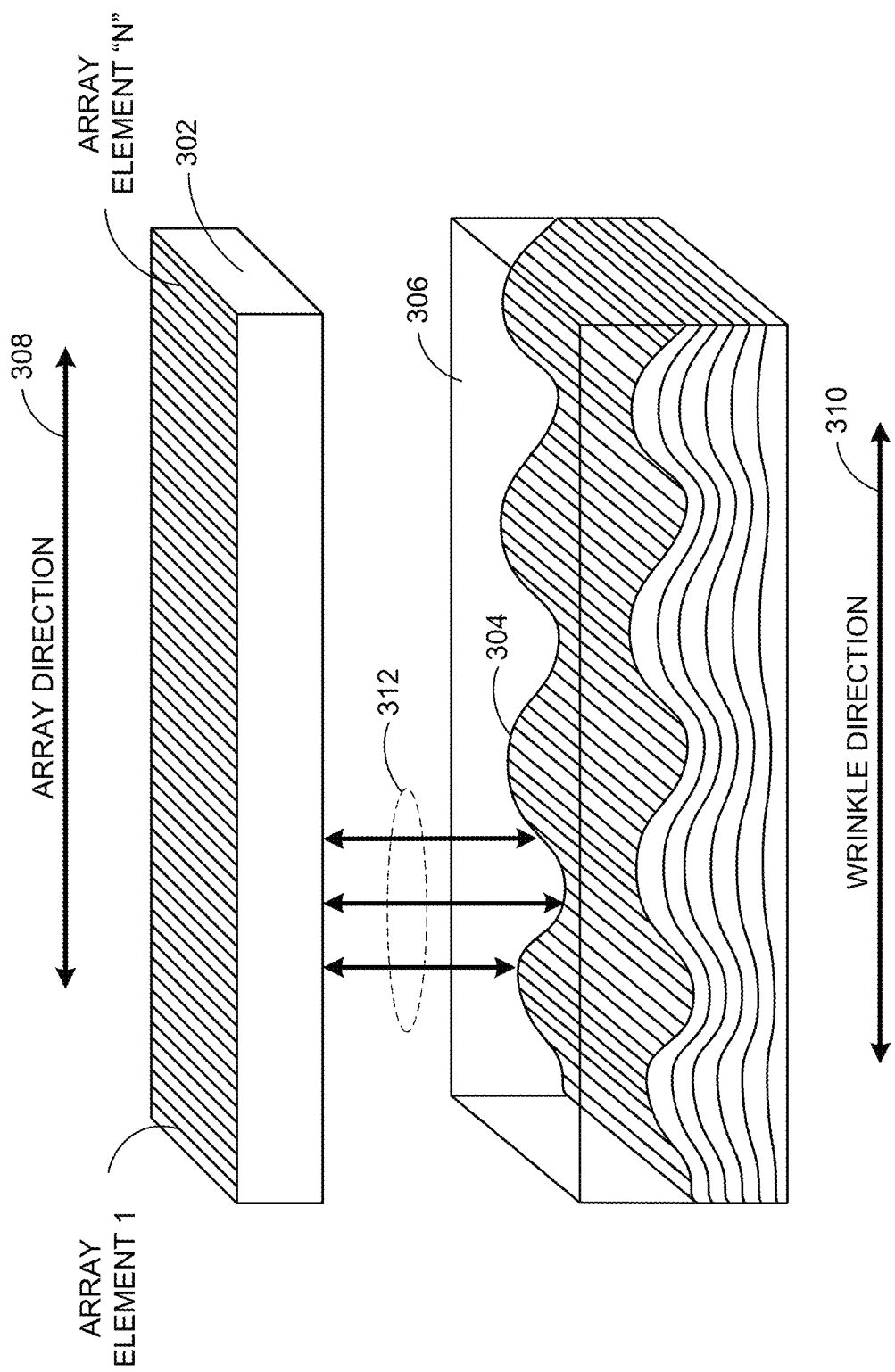
FIG. 3 illustrates an example transducer array oriented relative to an example wrinkle of an example composite laminate.

FIG. 3 illustrates an example transducer array 302 oriented relative to an example wrinkle 304 of an example composite laminate 306. The transducer array 302 of FIG. 3 may be implemented by the ultrasonic transducer 102 of FIG. 1. The transducer array 302 includes "N" number of array elements. For example, the transducer array 302 may include one hundred twenty-eight elements when N=128. The array elements of the transducer array are spaced apart and/or adjacently oriented along an example array direction 308 of the transducer array 302. The wrinkle 304 of the composite laminate 306 of FIG. 3 extends and/or is oriented along an example wrinkle direction 310. In some examples, the wrinkle direction 310 corresponds to an expected wrinkle direction, such as a chord wise direction of the composite laminate 306 or a span wise direction of the composite laminate 306.

In the illustrated example of FIG. 3, the transducer array 302 is positioned and/or oriented relative to the wrinkle 304 and/or relative to the composite laminate 306 such that the array direction 308 is generally parallel to the wrinkle direction 310. Positioning and/or orienting the transducer array 302 relative to the wrinkle 304 and/or the composite laminate 306 as shown in FIG. 3 advantageously places different ones of the array elements of the transducer array 302 at corresponding different example distances 312 away from the wrinkle 304 of the composite laminate 306, thereby improving the resolution of the imaging data for the wrinkle 304 to be captured by the transducer array 302 and/or by the ultrasonic transducer implementing the transducer array 302. In other examples, the transducer array 302 may be positioned and/or oriented relative to the wrinkle 304 and/or relative to the composite laminate 306 such that the array direction 308 is at an angle to (e.g., is not parallel to) the wrinkle direction 310.

Figure 4A:
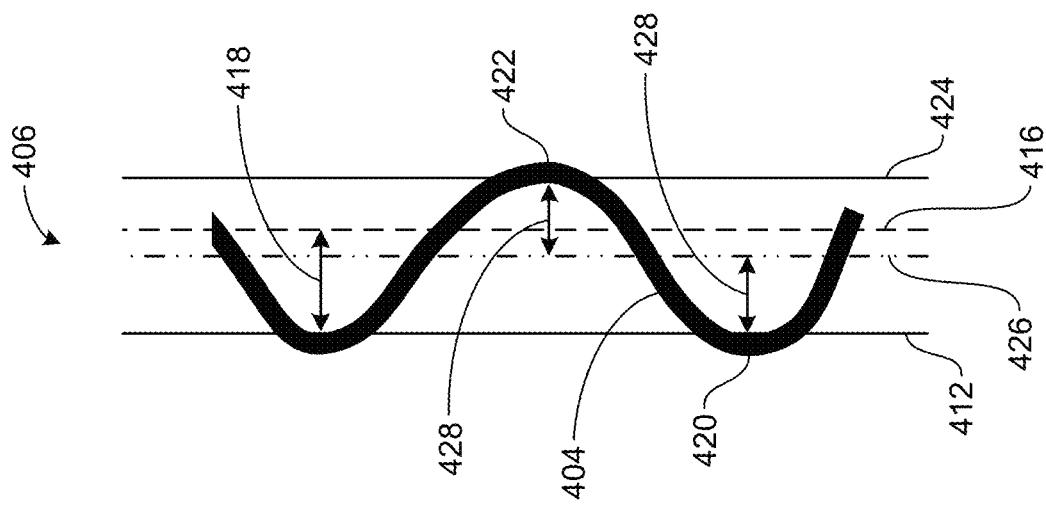
FIG. 4A is a schematic representing an example actual shape of an example out-of-plane wrinkle of a composite laminate.
Figure 4B:
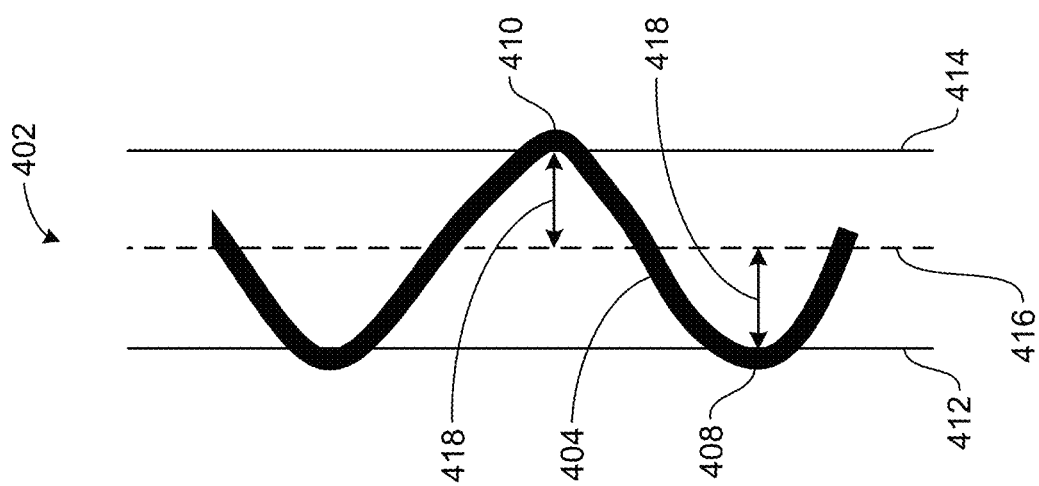
FIG. 4B is a schematic representing an example imaged shape of the example out-of-plane wrinkle of FIG. 4A.

FIG. 4A is a schematic representing an example actual shape 402 of an example out-of-plane wrinkle 404 of a composite laminate. FIG. 4B is a schematic representing an example imaged shape 406 of the example out-of-plane wrinkle 404 of FIG. 4A. The actual shape 402 of the out-of-plane wrinkle 404 of FIG. 4A may be visible, for example, via a destructive analysis that involves cutting and/or slicing into a composite laminate to reveal a cross-sectional segment and/or section of the composite laminate at which the out-of-plane wrinkle 404 is located. The imaged shape 406 of the out-of-plane wrinkle 404 of FIG. 4B may be visible, for example, via non-destructive ultrasonic scanning of the composite laminate as described above in connection with FIGS. 1 and 2.

In the illustrated example of FIG. 4A, the actual shape 402 of the out-of-plane wrinkle 404 is sinusoidal. For example, the actual shape 402 of the out-of-plane wrinkle 404 includes an example crest 408 and an example trough 410. In the illustrated example, the crest 408 may be directed toward a first and/or front side of the composite laminate (e.g., the first side 108 of the composite laminate 104 of FIG. 1), and the trough may be directed toward a second and/or back side of the composite laminate (e.g., the second side 110 of the composite laminate 104 of FIG. 1). The actual shape 402 of the out-of-plane wrinkle 404 is marked with an example crest line 412 associated with the crest 408 (e.g., positioned along an inside surface of the crest 408), an example trough line 414 associated with the trough 410 (e.g., positioned along an inside surface of the trough 410), and an example center line 416 located midway between the crest line 412 and the trough line 414. The actual shape 402 of the out-of-plane wrinkle 404 accordingly has an example amplitude 418 extending between the crest line 412 and the center line 416, and/or extending between the trough line 414 and the center line 416.

In the illustrated example of FIG. 4B, the imaged shape 406 of the out-of-plane wrinkle 404 is a modified sinusoidal shape (e.g., modified relative to the actual shape 402 of the out-of-plane wrinkle 404 described above in connection with FIG. 4A). For example, the imaged shape 406 of the out-of-plane wrinkle 404 includes an example imaged crest 420 and an example imaged trough 422. In the illustrated example, the imaged crest 420 may be directed toward a first side of the composite laminate (e.g., the first side 108 of the composite laminate 104 of FIG. 1), and the imaged trough 422 may be directed toward a second side of the composite laminate (e.g., the second side 110 of the composite laminate 104 of FIG. 1). When the out-of-plane wrinkle 404 is ultrasonically scanned from the first side of the composite laminate, the shape of the imaged crest 420 accurately represents (e.g., is substantially identical to) the actual shape of the crest 408. The shape of the imaged trough 422, however, does not accurately represent the actual shape of the trough 410 due to focusing and/or reflective effects caused by the concave shape of the imaged trough 422. As a result, while the imaged shape 406 of the out-of-plane wrinkle 404 may be correctly marked with the same crest line 412 associated with the crest 408, the imaged shape 406 may be incorrectly marked with an example imaged trough line 424 associated with the imaged trough 422, and incorrectly marked with an example imaged center line 426 located midway between the crest line 412 and the imaged trough line 424. The imaged shape 406 of the out-of-plane wrinkle 404 may accordingly have an example imaged amplitude 428 extending between the crest line 412 and the imaged center line 426, and/or extending between the imaged trough line 424 and the imaged center line 426.

As shown in the imaged shape 406 of the out-of-plane wrinkle 404 of FIG. 4B, the location of the imaged center line 426 does not match the location of the center line 416 associated with the actual shape 402 of the out-of-plane wrinkle 404, and the magnitude of the imaged amplitude 428 does not match the magnitude of the amplitude 418 associated with the actual shape 402 of the out-of-plane wrinkle 404. The methods disclosed herein provide for a compensation technique that allows the imaged shape 406 of the out-of-plane wrinkle 404 to be correctly and/or accurately marked with a center line corresponding to the center line 416 of the actual shape 402 of the out-of-plane wrinkle 404, such that an amplitude of the out-of-plane wrinkle 404 may be correctly and/or accurately measured from the imaged shape 406.

While the above-described example of FIG. 4B is directed to a scenario in which the out-of-plane wrinkle 404 is ultrasonically scanned from the first side of the composite laminate, a similar, but inversely related phenomenon is present when the same out-of-plane wrinkle 404 is ultrasonically scanned from the second side of the composite laminate instead of the first side. In such an example, a shape of an imaged trough of the out-of-plane wrinkle 404 would accurately represent the actual shape of the trough 410, but a shape of an imaged crest of the out-of-plane wrinkle 404 would not accurately represent the actual shape of the crest 408 due to focusing and/or reflective effects caused by the concave shape of the imaged crest. In such an example, an imaged shape of the out-of-plane wrinkle 404 may be correctly marked with the same trough line 414 associated with the trough 410, but the imaged shape may be incorrectly marked with an imaged crest line associated with the imaged crest, and incorrectly marked with an imaged center line located midway between the trough line 414 and the imaged crest line. In such an example, the methods disclosed herein provide for a compensation technique that allows the imaged shape of the out-of-plane wrinkle 404 to be correctly and/or accurately marked with a center line corresponding to the center line 416 of the actual shape 402 of the out-of-plane wrinkle 404, such that an amplitude of the out-of-plane wrinkle 404 may be correctly and/or accurately measured from the imaged shape.

Figure 5A:
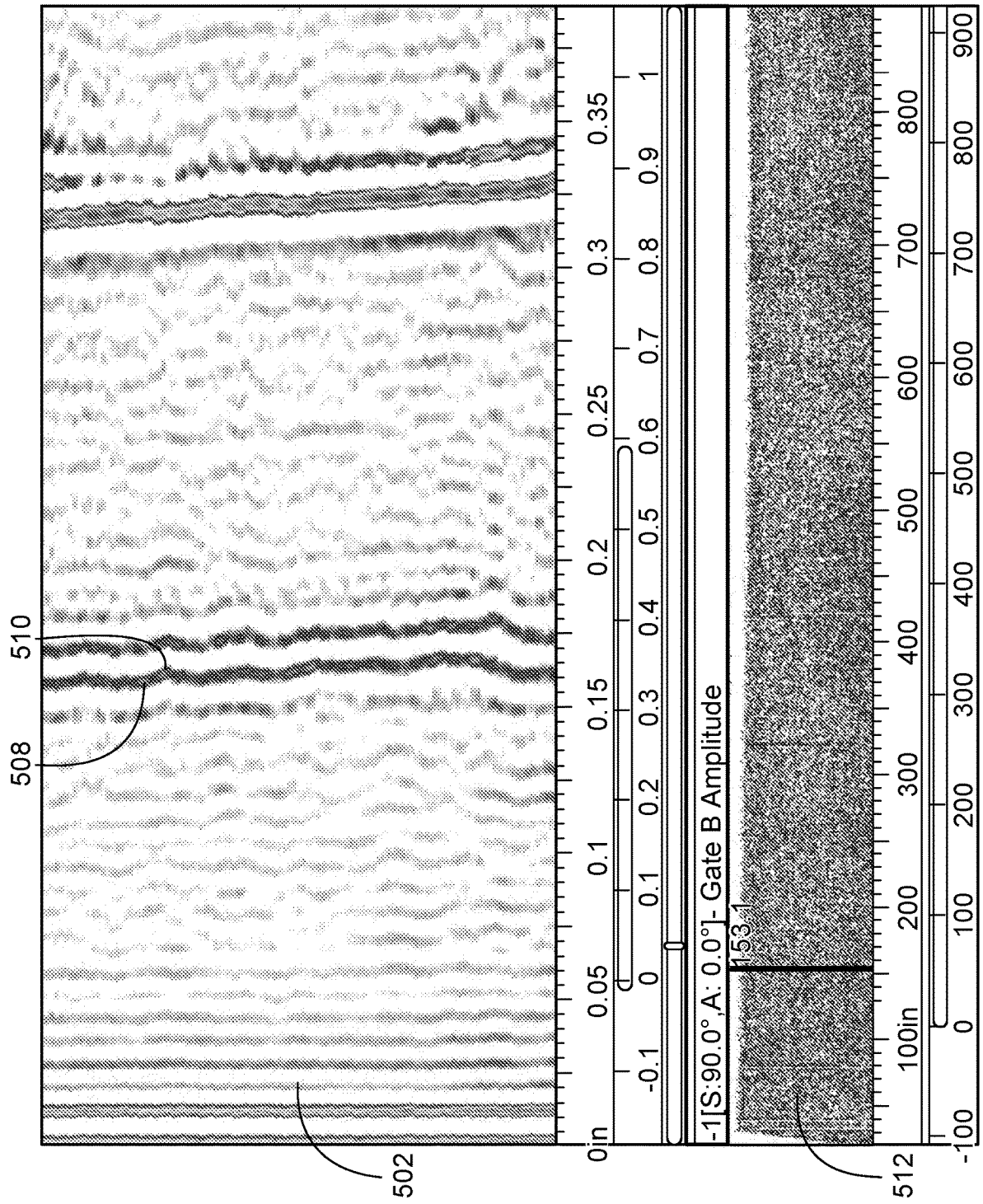
FIGS. 5A, 5B and 5C are respective first, second and third example B-scan ultrasound images from among an ordered series of B-scan ultrasound images generated in response to ultrasonically scanning a composite laminate.
Figure 5B:
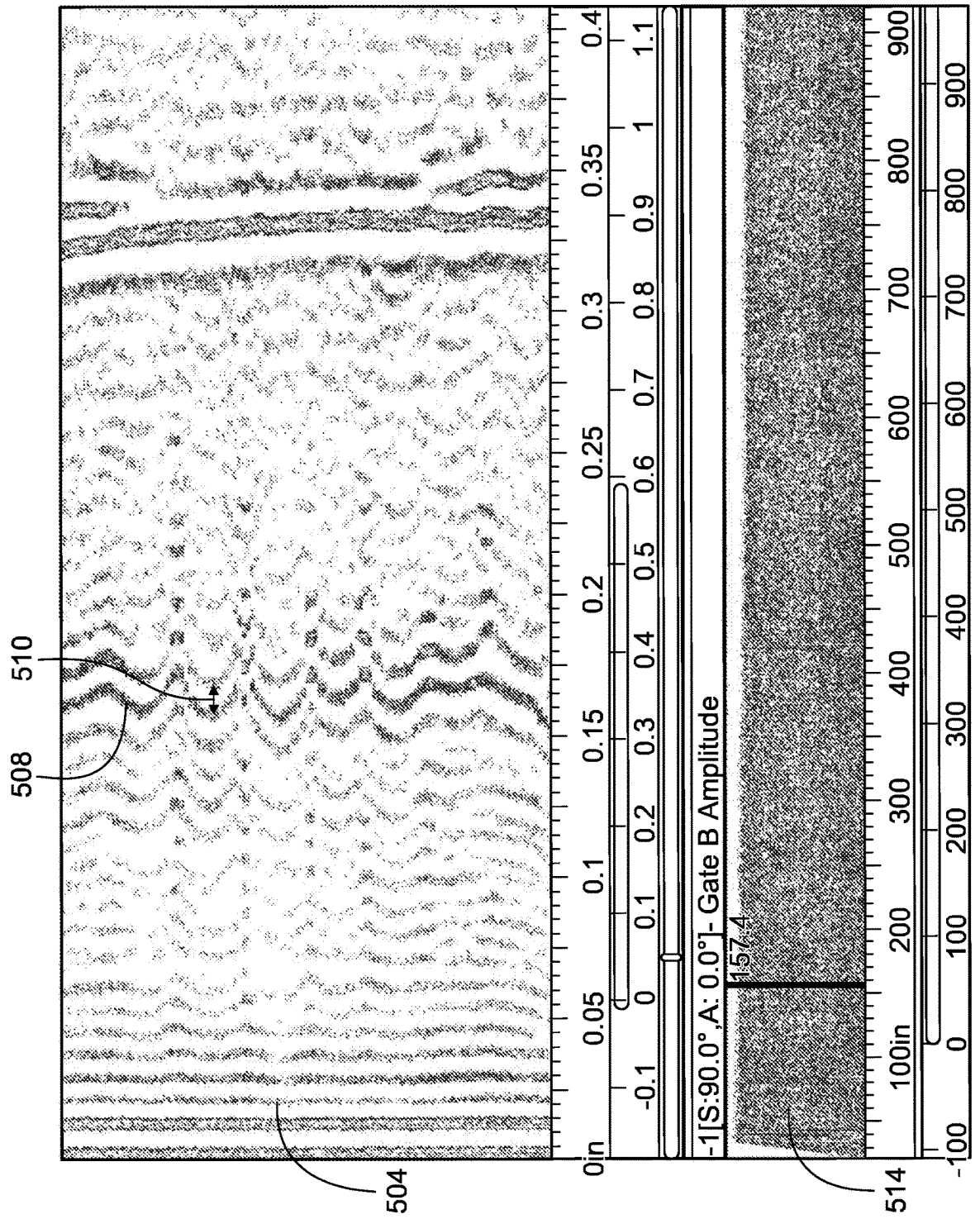
Figure 5C:
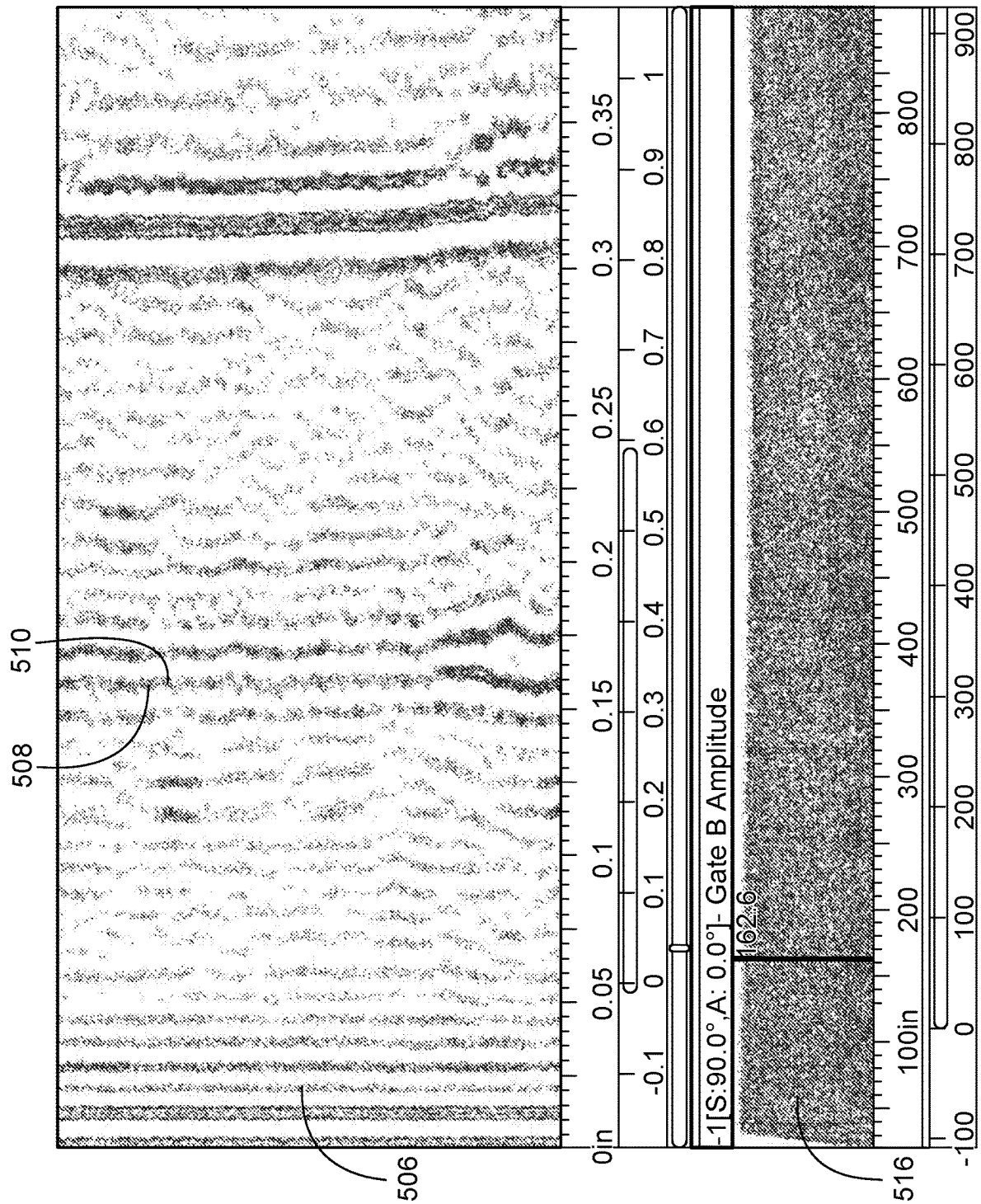

FIGS. 5A, 5B and 5C are respective first, second and third example B-scan ultrasound images 502, 504, 506 from among an ordered series of B-scan ultrasound images generated in response to ultrasonically scanning a composite laminate. For example, respective ones of the first, second and third B-scan ultrasound images 502, 504, 506 may be generated by the computer system 106 of FIG. 1 based on ultrasonic B-scan data acquired from and/or obtained via the ultrasonic transducer 102 of FIG. 1 scanning the first side 108 of the composite laminate 104 of FIG. 1. In other examples, respective ones of the first, second and third B-scan ultrasound images 502, 504, 506 may alternatively be generated by the computer system 106 of FIG. 1 based on ultrasonic B-scan data acquired from and/or obtained via the ultrasonic transducer 102 or the second ultrasonic transducer 114 of FIG. 1 scanning the second side 110 of the composite laminate 104 of FIG. 1.

In some examples, the ordered series of B-scan ultrasound images (e.g., including the first, second and third B-scan ultrasound images 502, 504, 506 of FIGS. 5A, 5B and 5C) may be reviewed and/or analyzed to identify and/or locate a most severe and/or a worst one of a plurality of out-of-plane wrinkles that may be present in the composite laminate. For example, an example first out-of-plane wrinkle 508 is present in each of the first, second and third B-scan ultrasound images 502, 504, 506 of FIGS. 5A, 5B and 5C. In the illustrated example of FIGS. 5A, 5B and 5C, an example amplitude 510 associated with the first out-of-plane wrinkle 508 has an increased value (e.g., a maximum value) on and/or at the second B-scan ultrasound image 504 of FIG. 5B. For example, the value of the amplitude 510 of the first out-of-plane wrinkle 508 is greater on and/or at the second B-scan ultrasound image 504 of FIG. 5B in comparison to the respective values of the amplitude 510 of the first out-of-plane wrinkle 508 on and/or at the first B-scan ultrasound image 502 of FIG. 5A and the third B-scan ultrasound image 506 of FIG. 5C. In some examples, the second B-scan ultrasound image 504 of FIG. 5B may be chosen or selected for the purpose of analyzing and/or measuring the first out-of-plane wrinkle 508. In some such examples, the selection of the second B-scan ultrasound image 504 may be based on the second B-scan ultrasound image 504 being the single B-scan ultrasound image from among the ordered series of B-scan ultrasound images at which the amplitude 510 of the first out-of-plane wrinkle 508 has a maximum value (e.g., at which the first out-of-plane wrinkle 508 is most severe).

In some examples, an ordered series of C-scan ultrasound images generated in response to ultrasonically scanning a composite laminate may be correlated with the B-scan ultrasound images generated in response to ultrasonically scanning the composite laminate. For example, as shown in FIG. 5A, a first example C-scan ultrasound image 512 is correlated with the first B-scan ultrasound image 502. The first C-scan ultrasound image 512 may be used to identify the location of the first out-of-plane wrinkle 508 shown on and/or at the first B-scan ultrasound image 502 of FIG. 5A along a C-plane of the composite laminate. Similarly, as shown in FIG. 5B, a second example C-scan ultrasound image 514 is correlated with the second B-scan ultrasound image 504. The second C-scan ultrasound image 514 may be used to identify the location of the first out-of-plane wrinkle 508 shown on and/or at the second B-scan ultrasound image 504 of FIG. 5B along the C-plane of the composite laminate. Similarly, as shown in FIG. 5C, a third example C-scan ultrasound image 516 is correlated with the third B-scan ultrasound image 506. The third C-scan ultrasound image 516 may be used to identify the location of the first out-of-plane wrinkle 508 shown on and/or at the third B-scan ultrasound image 506 of FIG. 5C along the C-plane of the composite laminate.

In some examples, identifying the location of the first out-of-plane wrinkle 508 along the C-plane of the composite laminate based on a particular one of the ordered series of B-scan ultrasound images enables the location of the first out-of-plane wrinkle 508 to be marked (e.g., physically marked with a marking pen or a similar marking device) on the first side 108 (or, in other examples, on the second side 110) of the composite laminate 104. For example, it may be desirable to mark the location of the most severe and/or the worst out-of-plane wrinkle of the composite laminate 104 on the first side 108 and/or the second side 110 of the composite laminate. In such an example, the location to be marked on the composite laminate 104 may be identified based on the correlation between the second C-scan ultrasound image 514 of FIG. 5B and the second B-scan ultrasound image 504 of FIG. 5B, which is the location along the C-plane of the composite laminate 104 where the amplitude 510 of the first out-of-plane wrinkle 508 has an increased and/or maximum value (e.g., where the first out-of-plane wrinkle 508 is most severe). The marking of the composite laminate 104 may be based on the identified location.

Figure 6:
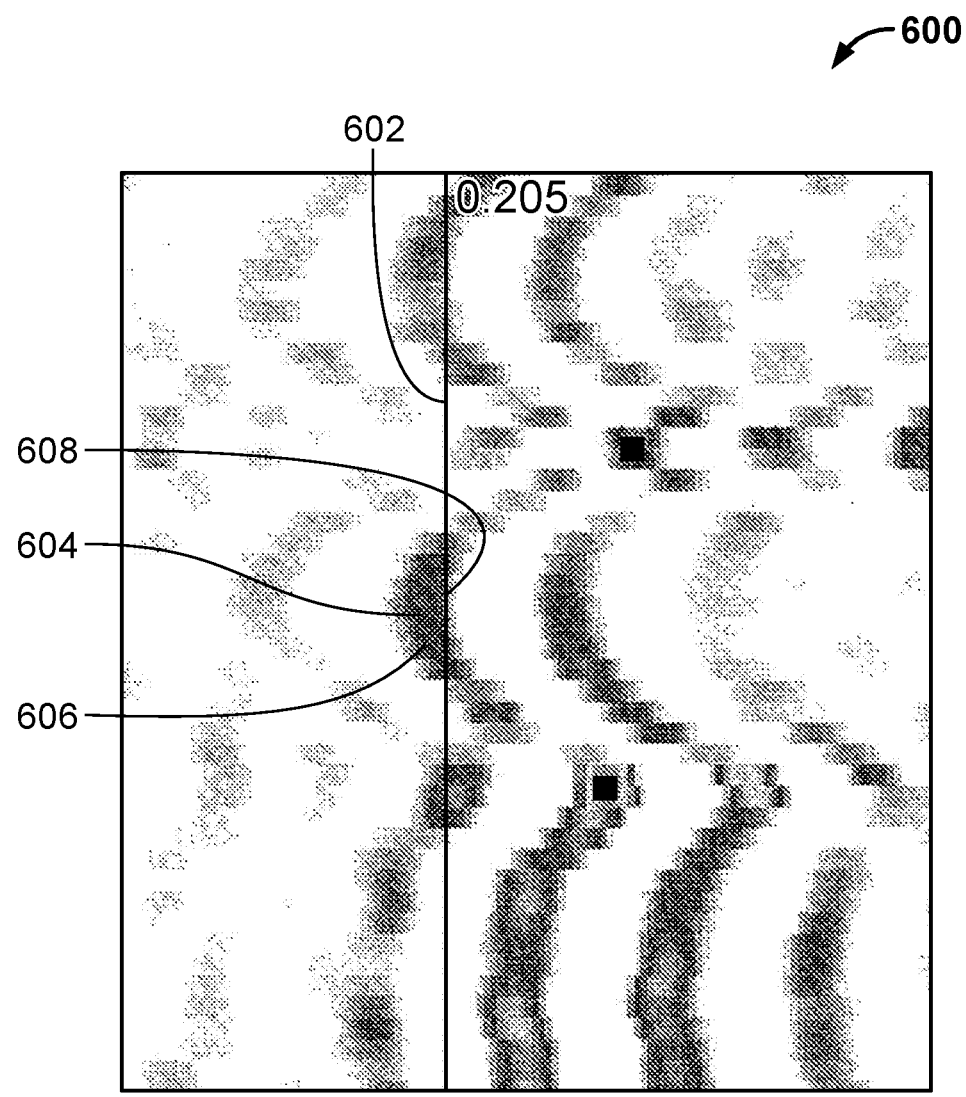
FIG. 6 is an example B-scan ultrasound image including an example crest line marker corresponding to a location of an example crest of an example out-of-plane wrinkle of a composite laminate.

FIG. 6 is an example B-scan ultrasound image 600 including an example crest line marker 602 corresponding to a location of an example crest 604 of an example out-of-plane wrinkle 606 of a composite laminate. The B-scan ultrasound image 600 of FIG. 6 may be generated and displayed via the computer system 106 of FIG. 1 based on ultrasonic B-scan data obtained and/or acquired via the ultrasonic transducer 102 of FIG. 1. For example, the B-scan ultrasound image 600 of FIG. 6 corresponds to ultrasonic B-scan data associated with the ultrasonic transducer 102 scanning the first side 108 of the composite laminate 104 of FIG. 1. In some examples, the out-of-plane wrinkle 606 is a most severe and/or worst one from among a plurality of out-of-plane wrinkles included in the B-scan ultrasound image 600 of FIG. 6. In some examples, the out-of-plane wrinkle 606 has a maximum amplitude at and/or on the B-scan ultrasound image 600 of FIG. 6 relative to the respective amplitudes of the same out-of-plane wrinkle 606 on other B-scan ultrasound images of the same composite laminate.

In the illustrated example of FIG. 6, the crest 604 of the out-of-plane wrinkle 606 is directed toward the first side 108 of the composite laminate 104. The crest line marker 602 is positioned and/or located along an example inside surface 608 of the crest 604 of the out-of-plane wrinkle 606. In some examples, the crest line marker 602 may be applied to and/or located on and/or over the B-scan ultrasound image 600 of FIG. 6 based on one or more instruction(s) and/or command(s) provided to the computer system 106 of FIG. 1 by an operator (e.g., an end user). In some examples, the crest line marker 602 is electronically applied to or over the B-scan ultrasound image 600 of FIG. 6. For example, the crest line marker 602 of FIG. 6 may be a straight-line measurement cursor cable of being electronically applied to the B-scan ultrasound image 600 of FIG. 6 via the computer system 106 of FIG. 1.

Figure 7:
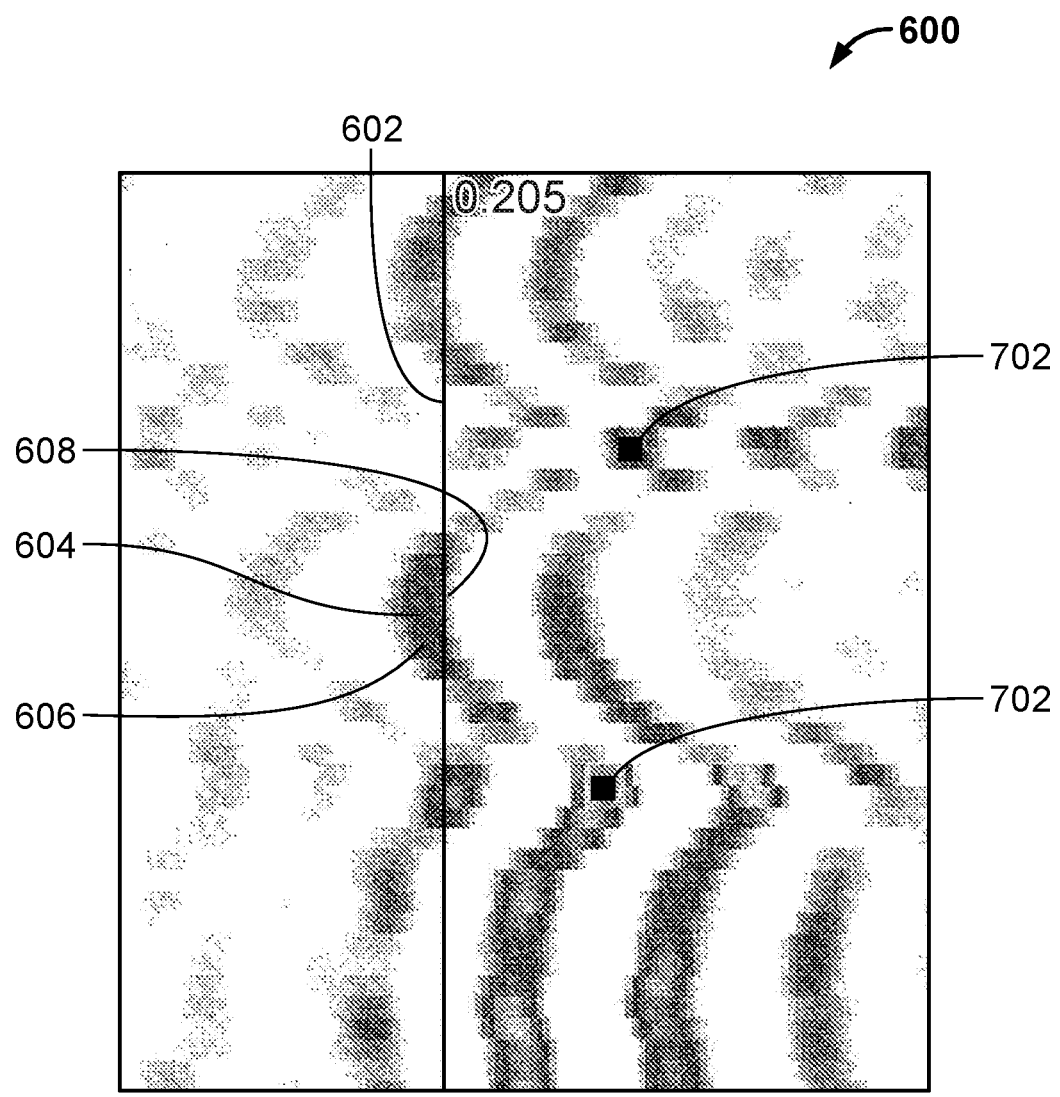
FIG. 7 is the example B-scan ultrasound image of FIG. 6 illustrating example trough focal points of the example out-of-plane wrinkle of FIG. 6.

FIG. 7 is the example B-scan ultrasound image 600 of FIG. 6 illustrating example trough focal points 702 of the example out-of-plane wrinkle 606 of FIG. 6. The trough focal points 702 of FIG. 7 appear on the B-scan ultrasound image 600 as a result of focusing and/or reflective effects caused by a concave shape of a trough of the out-of-plane wrinkle 606, as explained above in connection with FIGS. 4A and 4B. In some examples, respective ones of the trough focal points 702 of the out-of-plane wrinkle 606 are indicated graphically and/or visually in the B-scan ultrasound image 600 by a data point that is sharp and/or focused relative to the data corresponding to the other portions (e.g., the crest 604, etc.) of the out-of-plane wrinkle 606. Identifying the respective locations of the trough focal points 702 facilitates the proper and/or correct placement of a center line for the out-of-plane wrinkle 606 on the B-scan ultrasound image 600.

Figure 8:
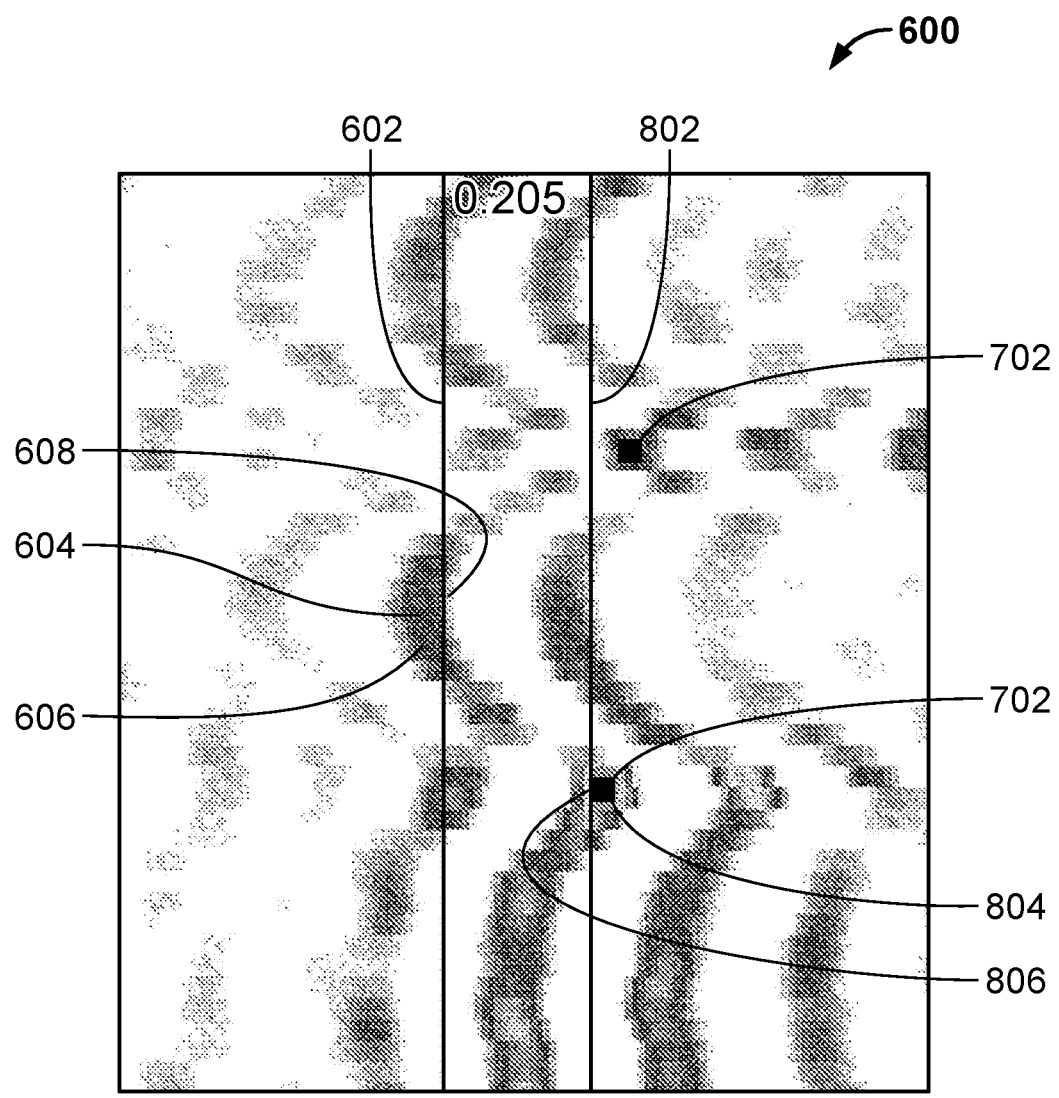
FIG. 8 is the example B-scan ultrasound image of FIG. 7 including an example center line marker corresponding to a location of a center line of the example out-of-plane wrinkle of FIGS. 6 and 7.

FIG. 8 is the example B-scan ultrasound image 600 of FIG. 7 including an example center line marker 802 corresponding to a location of a center line of the example out-of-plane wrinkle 606 of FIGS. 6 and 7. In the illustrated example of FIG. 8, the center line marker 802 is positioned and/or located along a first example one 804 of the trough focal points 702 of the out-of-plane wrinkle 606. In some examples, the first one 804 of the trough focal points 702 is the trough focal point from among the trough focal points 702 that is closest and/or most proximate to the crest line marker 602 applied to the B-scan ultrasound image 600. In some examples, the center line marker 802 may be applied along an example inside surface 806 of the first one 804 of the trough focal points 702 such that the center line marker 802 is parallel to the crest line marker 602. In some examples, the center line marker 802 may be applied to and/or located on and/or over the B-scan ultrasound image 600 of FIG. 8 based on one or more instruction(s) and/or command(s) provided to the computer system 106 of FIG. 1 by an operator (e.g., an end user). In some examples, the center line marker 802 is electronically applied to or over the B-scan ultrasound image 600 of FIG. 8. For example, the center line marker 802 of FIG. 8 may be a straight-line measurement cursor cable of being electronically applied to the B-scan ultrasound image 600 of FIG. 8 via the computer system 106 of FIG. 1.

Figure 9:
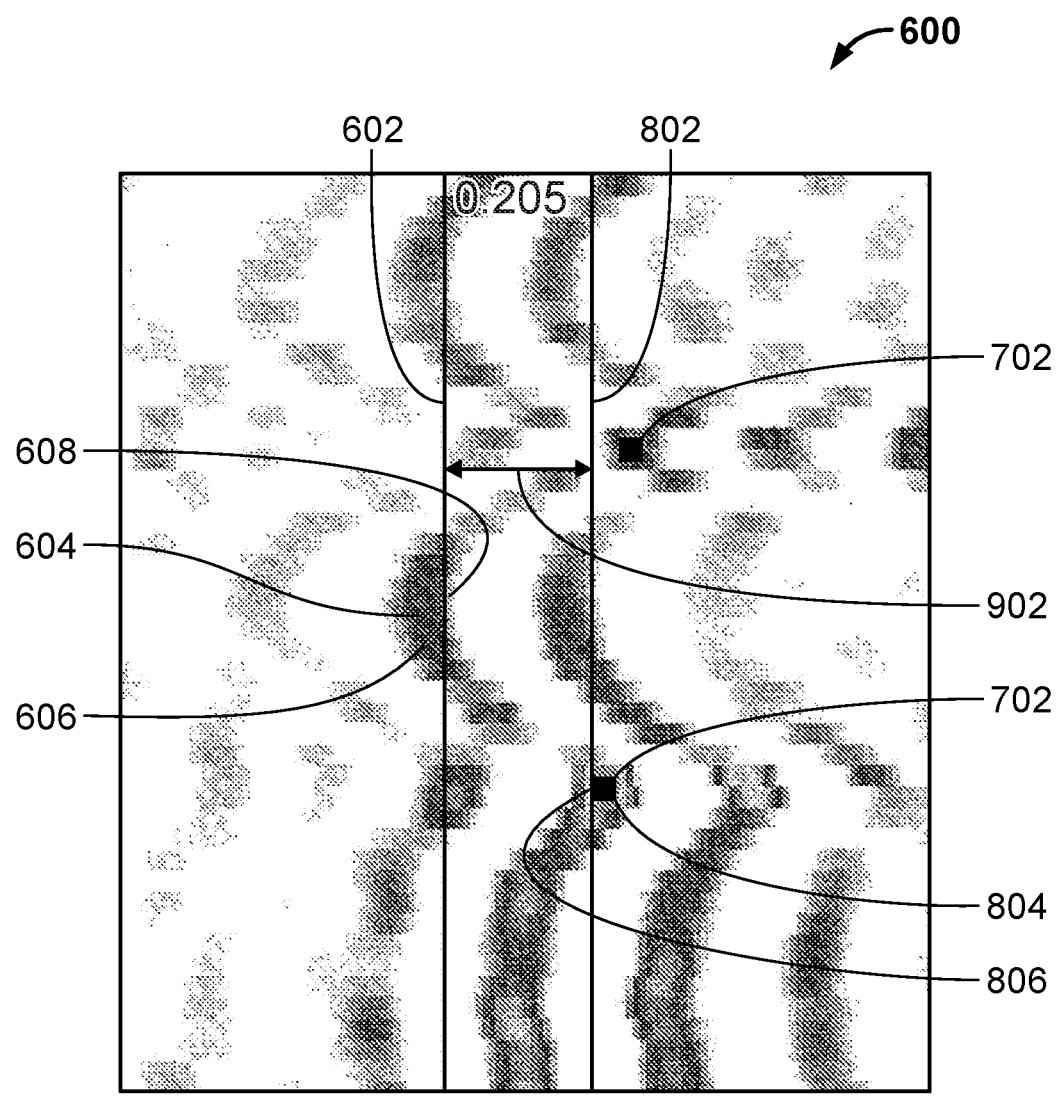
FIG. 9 is the example B-scan ultrasound image of FIG. 8 including an example distance marker corresponding to a distance between the example crest line marker of FIGS. 6-8 and the example center line marker of FIG. 8.

FIG. 9 is the example B-scan ultrasound image 600 of FIG. 8 including an example distance marker 902 corresponding to a distance between the example crest line marker 602 of FIGS. 6-8 and the example center line marker 802 of FIG. 8. In the illustrated example of FIG. 9, the distance marker 902 extends orthogonally to both the crest line marker 602 and the center line marker 802. In some examples, the distance marker 902 may be applied to and/or located on and/or over the B-scan ultrasound image 600 of FIG. 9 based on one or more instruction(s) and/or command(s) provided to the computer system 106 of FIG. 1 by an operator (e.g., an end user). In some examples, the distance marker 902 is electronically applied to or over the B-scan ultrasound image 600 of FIG. 9. For example, the distance marker 902 of FIG. 9 may be a straight-line measurement cursor cable of being electronically applied to the B-scan ultrasound image 600 of FIG. 9 via the computer system 106 of FIG. 1.

In the illustrated example of FIG. 9, a distance value associated with the distance marker 902 represents, indicates, and/or is equal to an amplitude of the out-of-plane wrinkle 606. Thus, the amplitude of the out-of-plane wrinkle 606 may be determined based on the distance value associated with the distance marker 902 of FIG. 9. In some examples, a height of the out-of-plane wrinkle 606 may be determined by doubling the amplitude of the out-of-plane wrinkle 606 (e.g., doubling the distance value associated with the distance marker 902 of FIG. 9).

In some examples, the operations described above in connection with FIGS. 1, 2, 5A, 5B, 5C and 6-9 may be repeated and/or alternatively applied in relation to a B-scan ultrasound image corresponding to ultrasonic B-scan data associated with the ultrasonic transducer 102 or the second ultrasonic transducer 114 of FIG. 1 scanning the second side 110 of the composite laminate 104 of FIG. 1. In some such examples, the above description pertaining to the crest line marker 602 and the crest 604 of the out-of-plane wrinkle 606 of FIGS. 6-9 may conversely apply to a trough line marker and a trough of the same out-of-plane wrinkle 606. In some such examples, the above description pertaining to the trough focal points 702 of the out-of-plane wrinkle 606 of FIGS. 7-9 may conversely apply to crest focal points of the same out-of-plane wrinkle 606. In some such examples, the above description pertaining to the center line marker 802 determined based on the first one 804 of the trough focal points 702 of the out-of-plane wrinkle 606 of FIGS. 8 and 9 may conversely apply to a second center line marker determined based on a first one of the crest focal points of the same out-of-plane wrinkle 606. In some such examples, the above description pertaining to the distance marker 902 of FIG. 9 corresponding to a distance between the crest line marker 602 of FIGS. 6-8 and the center line marker 802 of FIG. 8 may conversely apply to a second distance marker corresponding to a distance between the trough line marker and the second center line marker.

In some such examples, a distance value associated with the second distance marker may represent, indicate, and/or be equal to a second amplitude of the same out-of-plane wrinkle 606. Thus, the second amplitude of the out-of-plane wrinkle 606 may be determined based on the distance value associated with the second distance marker. In some such examples, a height of the out-of-plane wrinkle 606 may be determined by doubling the second amplitude of the out-of-plane wrinkle 606 (e.g., doubling the distance value associated with the second distance marker). In other such examples, a height of the out-of-plane wrinkle 606 may be determined by summing together the distance value and/or amplitude associated with the distance marker 902 of FIG. 9 and the distance value and/or second amplitude associated with the second distance marker.

The operations described above in connection with FIGS. 1, 2, 5A, 5B, 5C and 6-9 may be performed without physically altering the subject composite laminate (e.g., the composite laminate that is being evaluated). Accordingly, amplitudes and/or heights of out-of-plane wrinkles included in the subject composite laminate may advantageously be measured, calculated, and/or determined in a non-destructive manner. The disclosed non-destructive measurement techniques may be especially useful for qualifying and/or certifying that the subject composite laminate does not include out-of-plane wrinkles exceeding a specified and/or threshold height.

Figure 10:
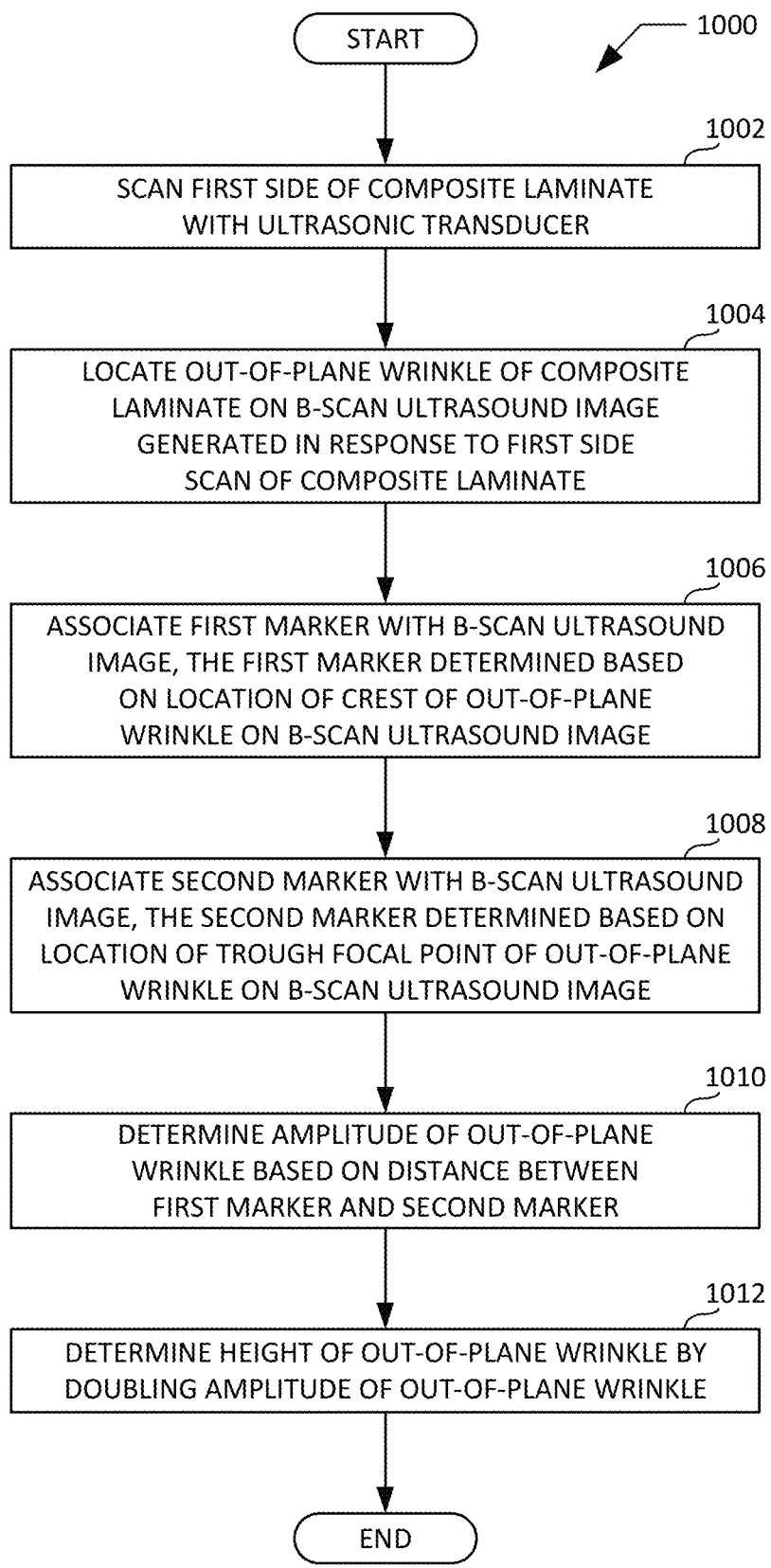
FIG. 10 is a flowchart representative of a first example method that may be implemented to measure out-of-plane wrinkles in composite laminates.
Figure 11A:
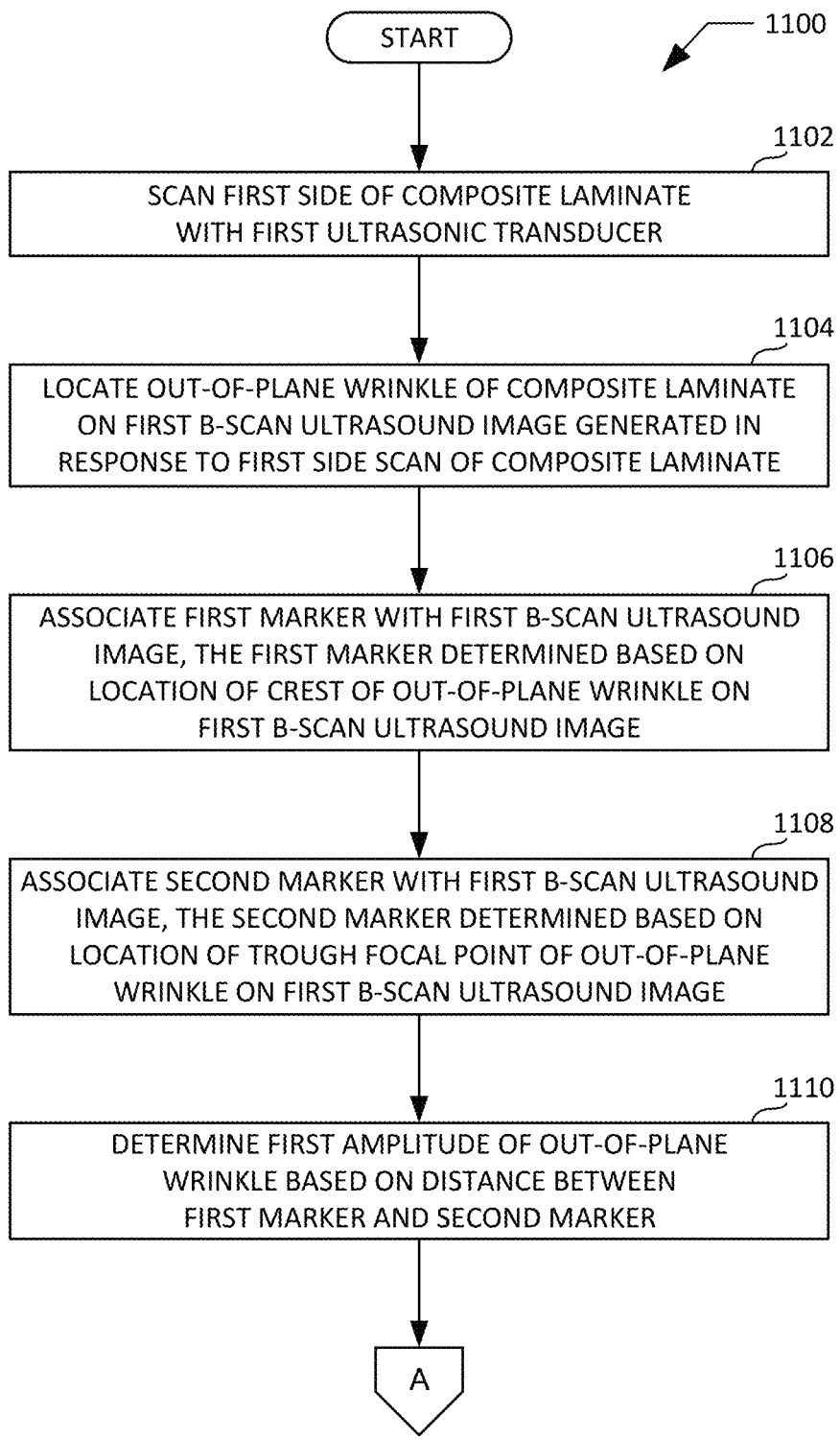
FIGS. 11A and 11B are a flowchart representative of a second example method that may be implemented to measure out-of-plane wrinkles in composite laminates.
Figure 11B:
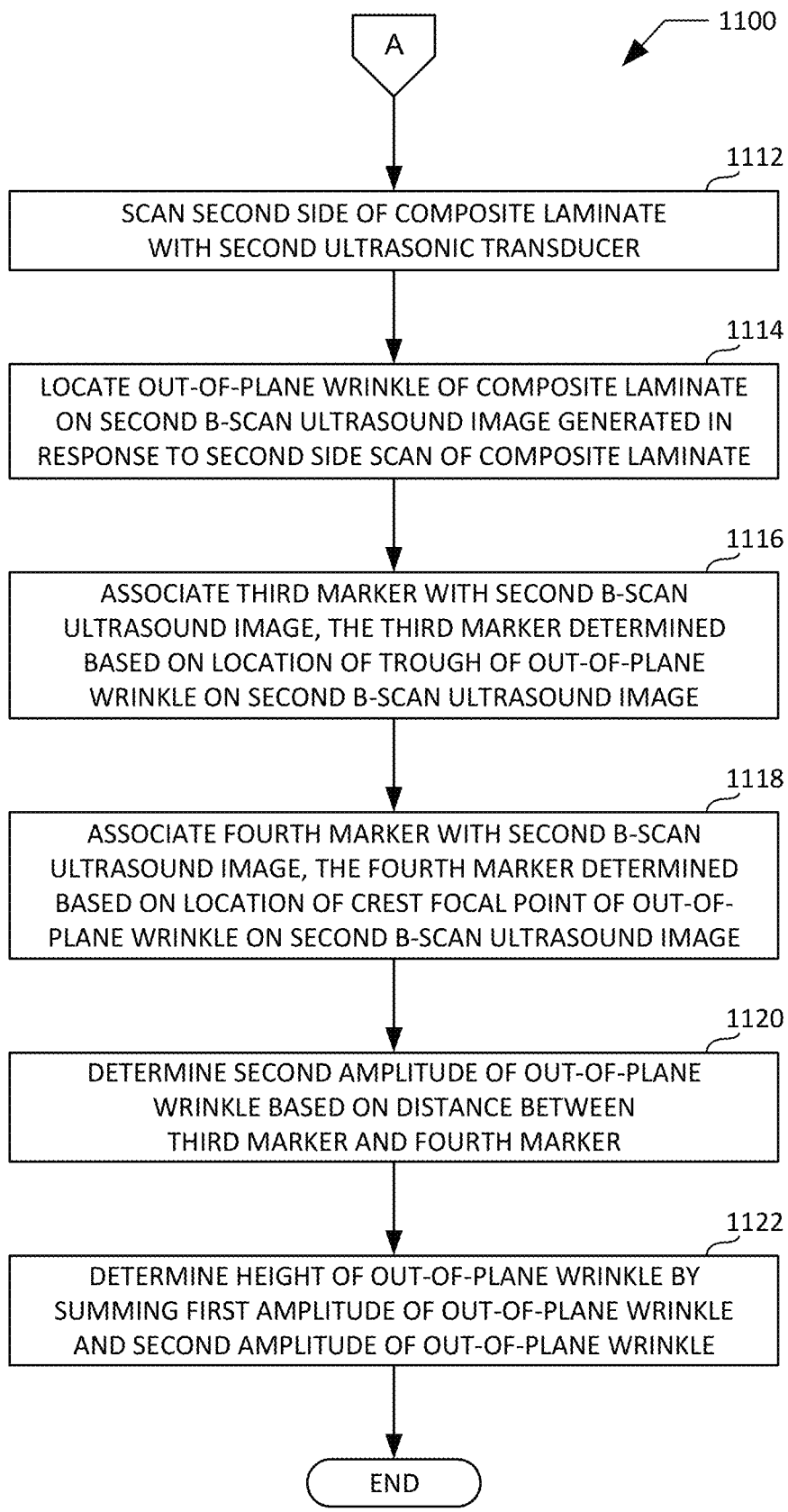

Flowcharts representative of example methods for measuring out-of-plane wrinkles in composite laminates are shown in FIGS. 10, 11A and 11B. In these examples, parts, portions and/or the entirety of the described methods may be implemented based on instructions and/or commands provided to the computer system 106 of FIG. 1 by an operator (e.g., an end user). Parts, portions and/or the entirety of the described methods may additionally or alternatively be implemented using machine-readable instructions that comprise one or more program(s) for execution by one or more processor(s) of the computer system 106 of FIG. 1 such as the processor 1202 shown in the example processor platform 1200 discussed below in connection with FIG. 12. The one or more program(s) may be embodied in software stored on a non-transitory computer readable storage medium such as a CD-ROM, a floppy disk, a hard drive, a digital versatile disk (DVD), a Blu-ray disk, or a memory associated with the processor 1202, but the entirety of any program and/or parts thereof could alternatively be executed by a device other than the processor 1202, and/or embodied in firmware or dedicated hardware. Further, although the example program(s) is/are described with reference to the flowcharts illustrated in FIGS. 10, 11A and 11B, many other methods for measuring out-of-plane wrinkles in composite laminates may alternatively be used. For example, the order of execution of the blocks may be changed, and/or some of the blocks described may be changed, eliminated, or combined. Additionally or alternatively, any or all of the blocks may be implemented by one or more hardware circuits (e.g., discrete and/or integrated analog and/or digital circuitry, a Field Programmable Gate Array (FPGA), an Application Specific Integrated circuit (ASIC), a comparator, an operational-amplifier (op-amp), a logic circuit, etc.) structured to perform the corresponding operation without executing software or firmware.

As mentioned above, the example methods of FIGS. 10, 11A and 11B may be implemented using coded instructions (e.g., computer and/or machine-readable instructions) stored on a non-transitory computer and/or machine-readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. "Including" and "comprising" (and all forms and tenses thereof) are used herein to be open ended terms. Thus, whenever a claim lists anything following any form of "include" or "comprise" (e.g., comprises, includes, comprising, including, etc.), it is to be understood that additional elements, terms, etc. may be present without falling outside the scope of the corresponding claim. As used herein, when the phrase "at least" is used as the transition term in a preamble of a claim, it is open-ended in the same manner as the term "comprising" and "including" are open ended.

FIG. 10 is a flowchart representative of a first example method 1000 for measuring an out-of-plane wrinkle in a composite laminate. The example method 1000 of FIG. 10 includes scanning a first side of a composite laminate with an ultrasonic transducer (block 1002). For example, the first side 108 of the composite laminate 104 of FIG. 1 may be scanned via the ultrasonic transducer 102 of FIG. 1.

The example method 1000 of FIG. 10 also includes locating an out-of-plane wrinkle of the composite laminate on a B-scan ultrasound image generated in response to the scanning of the first side of the composite laminate (block 1004). For example, the out-of-plane wrinkle 606 of the composite laminate 104 may be located on the B-scan ultrasound image 600 of FIG. 6. In such an example, the B-scan ultrasound image 600 of FIG. 6 may be generated by the computer system 106 of FIG. 1 based on ultrasonic B-scan data obtained and/or acquired via the ultrasonic transducer 102 scanning the first side 108 of the composite laminate 104.

The example method 1000 of FIG. 10 also includes associating a first marker with the B-scan ultrasound image, the first marker being determined based on a location of a crest of the out-of-plane wrinkle on the B-scan ultrasound image (block 1006). For example, the crest line marker 602 of FIG. 6 may be applied to and/or positioned over the B-scan ultrasound image 600 of FIG. 6. In such an example, the crest line marker 602 may be applied to and/or positioned over the B-scan ultrasound image 600 of FIG. 6 based on a location of the crest 604 of the out-of-plane wrinkle 606 on the B-scan ultrasound image 600 of FIG. 6.

The example method 1000 of FIG. 10 also includes associating a second marker with the B-scan ultrasound image, the second marker being determined based on a location of a trough focal point of the out-of-plane wrinkle on the B-scan ultrasound image (block 1008). For example, the center line marker 802 of FIG. 8 may be applied to and/or positioned over the B-scan ultrasound image 600 of FIG. 8. In such an example, the center line marker 802 may be applied to and/or positioned over the B-scan ultrasound image 600 of FIG. 8 based on a location of the first one 804 of the trough focal points 702 of the out-of-plane wrinkle 606 on the B-scan ultrasound image 600 of FIG. 8.

The example method 1000 of FIG. 10 also includes determining an amplitude of the out-of-plane wrinkle based on a distance between the first marker and the second marker (block 1010). For example, the distance marker 902 of FIG. 9 may be applied to and/or positioned over the B-scan ultrasound image 600 of FIG. 9. In such an example, the distance marker 902 may extend orthogonally to both the crest line marker 602 and the center line marker 802 of the B-scan ultrasound image 600 of FIG. 9. In such an example, a distance value associated with the distance marker 902 of FIG. 9 represents, indicates, and/or is equal to an amplitude of the out-of-plane wrinkle 606.

The example method 1000 of FIG. 10 also includes determining a height of the out-of-plane wrinkle by doubling the amplitude of the out-of-plane wrinkle (block 1012). For example, a height of the out-of-plane wrinkle 606 may be determined by doubling the amplitude of the out-of-plane wrinkle 606 (e.g., doubling the distance value associated with the distance marker 902 of FIG. 9). Following block 1012, the example method 1000 of FIG. 10 ends.

FIGS. 11A and 11B are a flowchart representative of a second example method 1100 for measuring an out-of-plane wrinkle in a composite laminate. The example method 1100 of FIGS. 11A and 11B includes scanning a first side of a composite laminate with a first ultrasonic transducer (block 1102). For example, the first side 108 of the composite laminate 104 of FIG. 1 may be scanned via the ultrasonic transducer 102 of FIG. 1.

The example method 1100 of FIGS. 11A and 11B also includes locating an out-of-plane wrinkle of the composite laminate on a first B-scan ultrasound image generated in response to the scanning of the first side of the composite laminate (block 1104). For example, the out-of-plane wrinkle 606 of the composite laminate 104 may be located on the B-scan ultrasound image 600 of FIG. 6. In such an example, the B-scan ultrasound image 600 of FIG. 6 may be generated by the computer system 106 of FIG. 1 based on ultrasonic B-scan data obtained and/or acquired via the ultrasonic transducer 102 scanning the first side 108 of the composite laminate 104.

The example method 1100 of FIGS. 11A and 11B also includes associating a first marker with the first B-scan ultrasound image, the first marker being determined based on a location of a crest of the out-of-plane wrinkle on the first B-scan ultrasound image (block 1106). For example, the crest line marker 602 of FIG. 6 may be applied to and/or positioned over the B-scan ultrasound image 600 of FIG. 6. In such an example, the crest line marker 602 may be applied to and/or positioned over the B-scan ultrasound image 600 of FIG. 6 based on a location of the crest 604 of the out-of-plane wrinkle 606 on the B-scan ultrasound image 600 of FIG. 6.

The example method 1100 of FIGS. 11A and 11B also includes associating a second marker with the first B-scan ultrasound image, the second marker being determined based on a location of a trough focal point of the out-of-plane wrinkle on the first B-scan ultrasound image (block 11008). For example, the center line marker 802 of FIG. 8 may be applied to and/or positioned over the B-scan ultrasound image 600 of FIG. 8. In such an example, the center line marker 802 may be applied to and/or positioned over the B-scan ultrasound image 600 of FIG. 8 based on a location of the first one 804 of the trough focal points 702 of the out-of-plane wrinkle 606 on the B-scan ultrasound image 600 of FIG. 8.

The example method 1100 of FIGS. 11A and 11B also includes determining a first amplitude of the out-of-plane wrinkle based on a distance between the first marker and the second marker (block 1110). For example, the distance marker 902 of FIG. 9 may be applied to and/or positioned over the B-scan ultrasound image 600 of FIG. 9. In such an example, the distance marker 902 may extend orthogonally to both the crest line marker 602 and the center line marker 802 of the B-scan ultrasound image 600 of FIG. 9. In such an example, a distance value associated with the distance marker 902 of FIG. 9 (e.g., a first distance marker) represents, indicates, and/or is equal to a first amplitude of the out-of-plane wrinkle 606.

The example method 1100 of FIGS. 11A and 11B includes scanning a second side of a composite laminate with a second ultrasonic transducer (block 1112). For example, the second side 110 of the composite laminate 104 of FIG. 1 may be scanned via the ultrasonic transducer 102 or the second ultrasonic transducer 114 of FIG. 1.

The example method 1100 of FIGS. 11A and 11B also includes locating the out-of-plane wrinkle of the composite laminate on a second B-scan ultrasound image generated in response to the scanning of the second side of the composite laminate (block 1114). For example, the out-of-plane wrinkle 606 of the composite laminate 104 may be located on a B-scan ultrasound image generated by the computer system 106 of FIG. 1 based on ultrasonic B-scan data obtained and/or acquired via the ultrasonic transducer 102 or the second ultrasonic transducer 114 of FIG. 1 scanning the second side 110 of the composite laminate 104.

The example method 1100 of FIGS. 11A and 11B also includes associating a third marker with the second B-scan ultrasound image, the third marker being determined based on a location of a trough of the out-of-plane wrinkle on the second B-scan ultrasound image (block 1116). For example, a trough line marker may be applied to and/or positioned over the second B-scan ultrasound image based on a location of a trough of the out-of-plane wrinkle 606 on the second B-scan ultrasound image.

The example method 1100 of FIGS. 11A and 11B also includes associating a fourth marker with the second B-scan ultrasound image, the fourth marker being determined based on a location of a crest focal point of the out-of-plane wrinkle on the second B-scan ultrasound image (block 1118). For example, a center line marker may be applied to and/or positioned over the second B-scan ultrasound image based on a location of a first one of multiple crest focal points of the out-of-plane wrinkle 606 on the second B-scan ultrasound image.

The example method 1100 of FIGS. 11A and 11B also includes determining a second amplitude of the out-of-plane wrinkle based on a distance between the third marker and the fourth marker (block 1120). For example, a second distance marker may be applied to and/or positioned over the second B-scan ultrasound image. In such an example, the second distance marker may extend orthogonally to both the trough line marker and the center line marker of the second B-scan ultrasound image. In such an example, a distance value associated with the second distance marker represents, indicates, and/or is equal to a second amplitude of the out-of-plane wrinkle 606.

The example method 1100 of FIGS. 11A and 11B also includes determining a height of the out-of-plane wrinkle by summing together the first amplitude of the out-of-plane wrinkle and the second amplitude of the out-of-plane wrinkle (block 1122). For example, a height of the out-of-plane wrinkle 606 may be determined by summing together the first amplitude of the out-of-plane wrinkle 606 (e.g., the distance value associated with the distance marker 902 of FIG. 9) and the second amplitude of the out-of-plane wrinkle 606 (e.g., the distance value associated with the second distance marker). Following block 1122, the example method 1100 of FIGS. 11A and 11B ends.

Figure 12:
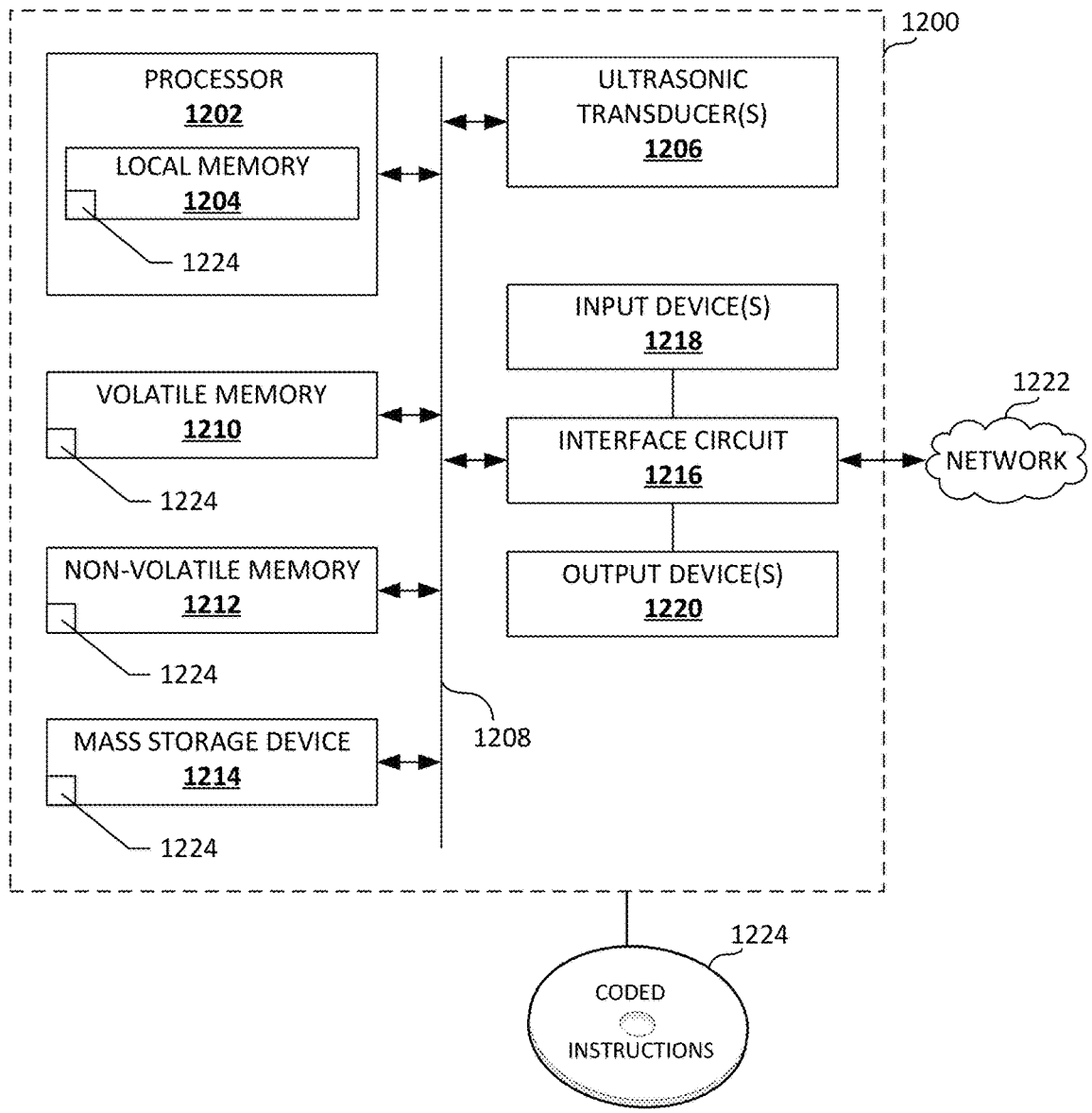
FIG. 12 is a block diagram of an example processor platform capable of executing instructions to implement the first example method of FIG. 10 and/or the second example method of FIGS. 11A and 11B.

FIG. 12 is a block diagram of an example processor platform 1200 capable of executing instructions to implement the first example method 1000 of FIG. 10 and/or the second example method 1100 of FIGS. 11A and 11B to measure out-of-plane wrinkles in composite laminates. The processor platform 1200 can be, for example, an ultrasound workstation, a desktop computer, a laptop computer, a server, a tablet, or any other type of computing device. In some examples, the example computer system 106 of FIG. 1 may include, and/or be implemented via, the processor platform 1200 of FIG. 12.

The processor platform 1200 of the illustrated example includes a processor 1202. The processor 1202 of the illustrated example is hardware. For example, the processor 1202 can be implemented by one or more integrated circuit(s), logic circuit(s), microprocessor(s) or controller(s) from any desired family or manufacturer.

The processor 1202 of the illustrated example is in communication with one or more ultrasonic transducer(s) 1206 via a bus 1208. In the example of FIG. 12, the ultrasonic transducer(s) 1206 may include the example ultrasonic transducer 102 and/or the second example ultrasonic transducer 114 of FIG. 1 described above.

The processor 1202 of the illustrated example is also in communication with a main memory including a volatile memory 1210 and a non-volatile memory 1212 via the bus 1208. The volatile memory 1210 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 1212 may be implemented by flash memory and/or any other desired type of memory device. Access to the volatile memory 1210 and the non-volatile memory 1212 is controlled by a memory controller.

The processor 1202 of the illustrated example is also in communication with a mass storage device 1214 for storing software and/or data. The mass storage device 1214 may be implemented, for example, via one or more floppy disk drives, hard drive disks, compact disk drives, Blu-ray disk drives, RAID systems, digital versatile disk (DVD) drives, etc.

The processor platform 1200 of the illustrated example also includes an interface circuit 1216. The interface circuit 1216 may be implemented by any type of interface standard, such as an Ethernet interface, a universal serial bus (USB), a Bluetooth® interface, a near field communication (NFC) interface, and/or a PCI express interface.

In the illustrated example, one or more input device(s) 1218 are connected to the interface circuit 1216. The input device(s) 1218 permit(s) a user to enter data and/or commands into the processor 1202. The input device(s) 1218 can be implemented by, for example, a keyboard, a button, a mouse, a touchscreen, a track-pad, a trackball, and/or a voice recognition system. One or more output device(s) 1220 are also connected to the interface circuit 1216 of the illustrated example. The output device(s) 1220 can be implemented, for example, by a display device (e.g., a light emitting diode (LED), an organic light emitting diode (OLED), a liquid crystal display (LCD), a cathode ray tube display (CRT), an in-place switching (IPS) display, a touchscreen, etc.), a tactile output device, a printer, and/or speaker. The interface circuit 1216 of the illustrated example, thus, typically includes a graphics driver card, a graphics driver chip and/or a graphics driver processor.

The interface circuit 1216 of the illustrated example also includes a communication device such as a transmitter, a receiver, a transceiver, a modem, a residential gateway, a wireless access point, and/or a network interface to facilitate exchange of data with external machines (e.g., computing devices of any kind) via a network 1222. The communication can be via, for example, an Ethernet connection, a digital subscriber line (DSL) connection, a telephone line connection, a coaxial cable system, a satellite system, a line-of-site wireless system, a cellular telephone system, etc.

Coded instructions 1224 for implementing the first example method 1000 of FIG. 10 and/or the second example method 1100 of FIGS. 11A and 11B may be stored in the local memory 1204, in the volatile memory 1210, in the non-volatile memory 1212, on the mass storage device 1214, and/or on a removable tangible computer readable storage medium such as a CD or DVD.

From the foregoing, it will be appreciated that the disclosed methods provide measurement techniques that advantageously enable out-of-plane wrinkles of composite laminates to be quantified in a non-destructive manner that does not physically alter the subject composite laminate. For example, the disclosed methods enable amplitudes and/or heights of out-of-plane wrinkles included in composite laminates to be measured, calculated, and/or determined in a non-destructive manner. The disclosed non-destructive measurement techniques may be especially useful for qualifying and/or certifying that the subject composite laminate does not include out-of-plane wrinkles exceeding a specified and/or threshold height.

In some examples, a method is disclosed. In some disclosed examples, the method comprises scanning a first side of a composite laminate with an ultrasonic transducer. In some disclosed examples, the method comprises locating an out-of-plane wrinkle of the composite laminate on a B-scan ultrasound image generated in response to the scanning of the first side of the composite laminate. In some disclosed examples, the method comprises associating a first marker with the B-scan ultrasound image. In some disclosed examples, the first marker is determined based on a location of a crest of the out-of-plane wrinkle on the B-scan ultrasound image. In some disclosed examples, the method comprises associating a second marker with the B-scan ultrasound image. In some disclosed examples, the second marker is determined based on a location of a trough focal point of the out-of-plane wrinkle on the B-scan ultrasound image. In some disclosed examples, the method comprises determining an amplitude of the out-of-plane wrinkle based on a distance between the first marker and the second marker.

In some disclosed examples, the method further comprises determining a height of the out-of-plane wrinkle by doubling the amplitude of the out-of-plane wrinkle.

In some disclosed examples of the method, the first marker is a crest line and the second marker is a center line.

In some disclosed examples of the method the associating of the first marker with the B-scan ultrasound image includes electronically applying the first marker to or over the B-scan ultrasound image, and the associating of the second marker with the B-scan ultrasound image includes electronically applying the second marker to or over the B-scan ultrasound image.

In some disclosed examples of the method, the composite laminate is not physically altered in response to any of the scanning of the first side of the composite laminate, the locating of the out-of-plane wrinkle, the associating of the first marker, the associating of the second marker, or the determining of the amplitude.

In some disclosed examples of the method, the out-of-plane wrinkle is a first one of a plurality of out-of-plane wrinkles on the B-scan ultrasound image. In some disclosed examples, the first one of the out-of-plane wrinkles has a maximum amplitude relative to respective amplitudes of corresponding other ones of the out-of-plane wrinkles.

In some disclosed examples of the method, the B-scan ultrasound image is a first one of a plurality of B-scan ultrasound images generated in response to the scanning of the first side of the composite laminate. In some disclosed examples, the out-of-plane wrinkle has a maximum amplitude on the first one of the B-scan ultrasound images relative to respective amplitudes of a same out-of-plane wrinkle on other ones of the B-scan ultrasound images.

In some disclosed examples, the method further comprises correlating a C-scan ultrasound image with the B-scan ultrasound image, the C-scan ultrasound image generated in response to the scanning of the first side of the composite laminate. In some disclosed examples, the method further comprises locating the out-of-plane wrinkle of the composite laminate on the C-scan ultrasound image based on the correlation between the C-scan ultrasound image and the B-scan ultrasound image. In some disclosed examples, the method further comprises marking the out-of-plane wrinkle on the first side of the composite laminate based on the location of the out-of-plane wrinkle on the B-scan ultrasound image and on the C-scan ultrasound image.

In some disclosed examples of the method, the composite laminate is a stringer for an aircraft.

In some examples, a method is disclosed. In some disclosed examples, the method comprises scanning a first side of a composite laminate with a first ultrasonic transducer. In some disclosed examples, the method comprises locating an out-of-plane wrinkle of the composite laminate on a first B-scan ultrasound image generated in response to the scanning of the first side of the composite laminate. In some disclosed examples, the method comprises associating a first marker with the first B-scan ultrasound image. In some disclosed examples, the first marker is determined based on a location of a crest of the out-of-plane wrinkle on the first B-scan ultrasound image. In some disclosed examples, the method comprises associating a second marker with the first B-scan ultrasound image. In some disclosed examples, the second marker is determined based on a location of a trough focal point of the out-of-plane wrinkle on the first B-scan ultrasound image. In some disclosed examples, the method comprises determining a first amplitude of the out-of-plane wrinkle based on a distance between the first marker and the second marker. In some disclosed examples, the method comprises scanning a second side of the composite laminate opposite the first side with a second ultrasonic transducer. In some disclosed examples, the method comprises locating the out-of-plane wrinkle of the composite laminate on a second B-scan ultrasound image generated in response to the scanning of the second side of the composite laminate. In some disclosed examples, the method comprises associating a third marker with the second B-scan ultrasound image. In some disclosed examples, the third marker is determined based on a location of a trough of the out-of-plane wrinkle on the second B-scan ultrasound image. In some disclosed examples, the method comprises associating a fourth marker with the second B-scan ultrasound image. In some disclosed examples, the fourth marker is determined based on a location of a crest focal point of the out-of-plane wrinkle on the second B-scan ultrasound image. In some disclosed examples, the method comprises determining a second amplitude of the out-of-plane wrinkle based on a distance between the third marker and the fourth marker.

In some disclosed examples, the method further comprises determining a height of the out-of-plane wrinkle by summing the first amplitude of the out-of-plane wrinkle and the second amplitude of the out-of-plane wrinkle.

In some disclosed examples of the method, the first marker is a crest line, the second marker is a first center line, the third marker is a trough line, and the fourth marker is a second center line.

In some disclosed examples of the method, the associating of the first marker with the first B-scan ultrasound image includes electronically applying the first marker to or over the first B-scan ultrasound image, the associating of the second marker with the first B-scan ultrasound image includes electronically applying the second marker to or over the first B-scan ultrasound image, the associating of the third marker with the second B-scan ultrasound image includes electronically applying the third marker to or over the second B-scan ultrasound image, and the associating of the fourth marker with the second B-scan ultrasound image includes electronically applying the fourth marker to or over the second B-scan ultrasound image.

In some disclosed examples of the method, the composite laminate is not physically altered in response to any of the scanning of the first side of the composite laminate, the locating of the out-of-plane wrinkle of the composite laminate on the first B-scan ultrasound image, the associating of the first marker, the associating of the second marker, the determining of the first amplitude, the scanning of the second side of the composite laminate, the locating of the out-of-plane wrinkle of the composite laminate on the second B-scan ultrasound image, the associating of the third marker, the associating of the fourth marker, or the determining of the second amplitude.

In some disclosed examples of the method, the out-of-plane wrinkle is a first one of a plurality of out-of-plane wrinkles on the first B-scan ultrasound image. In some disclosed examples, the first one of the out-of-plane wrinkles has a maximum amplitude relative to respective amplitudes of corresponding other ones of the out-of-plane wrinkles.

In some disclosed examples of the method, the first B-scan ultrasound image is a first one of a plurality of first B-scan ultrasound images generated in response to the scanning of the first side of the composite laminate. In some disclosed examples, the out-of-plane wrinkle has a maximum amplitude on the first one of the first B-scan ultrasound images relative to respective amplitudes of a same out-of-plane wrinkle on other ones of the first B-scan ultrasound images.

In some disclosed examples, the method further comprises correlating a first C-scan ultrasound image with the first B-scan ultrasound image, the first C-scan ultrasound image generated in response to the scanning of the first side of the composite laminate. In some disclosed examples, the method further comprises locating the out-of-plane wrinkle of the composite laminate on the first C-scan ultrasound image based on the correlation between the first C-scan ultrasound image and the first B-scan ultrasound image. In some disclosed examples, the method further comprises marking the out-of-plane wrinkle on the first side of the composite laminate based on the location of the out-of-plane wrinkle on the first B-scan ultrasound image and on the first C-scan ultrasound image.

In some disclosed examples of the method, the composite laminate is a stringer for an aircraft.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

What is claimed is:

1. A method for non-destructively determining an amplitude of an out-of-plane wrinkle of a composite laminate, the out-of-plane wrinkle located within the composite laminate between a first side of the composite laminate and a second side of the composite laminate, the second side located opposite the first side, the method comprising:
    scanning the first side of the composite laminate with an ultrasonic transducer;
    generating a B-scan ultrasound image based on ultrasonic B-scan data obtained via the ultrasonic transducer in response to the scanning of the first side;
    locating the out-of-plane wrinkle of the composite laminate on the B-scan ultrasound image;
    associating a first marker with the B-scan ultrasound image, the first marker being a crest line marker located along a crest of the out-of-plane wrinkle on the B-scan ultrasound image;
    associating a second marker with the B-scan ultrasound image, the second marker being a center line marker located along a trough focal point of the out-of-plane wrinkle on the B-scan ultrasound image; and
    determining the amplitude of the out-of-plane wrinkle based on a distance between the first marker and the second marker.

2. The method of claim 1, further comprising determining a height of the out-of-plane wrinkle by doubling the amplitude of the out-of-plane wrinkle.

3. The method of claim 1, wherein the associating of the first marker with the B-scan ultrasound image includes electronically applying the first marker to or over the B-scan ultrasound image, and the associating of the second marker with the B-scan ultrasound image includes electronically applying the second marker to or over the B-scan ultrasound image.

4. The method of claim 1, wherein the composite laminate is not physically altered in response to any of the scanning of the first side of the composite laminate, the generating of the B-scan ultrasound image, the locating of the out-of-plane wrinkle, the associating of the first marker, the associating of the second marker, or the determining of the amplitude.

5. The method of claim 1, wherein the out-of-plane wrinkle is a first one of a plurality of out-of-plane wrinkles on the B-scan ultrasound image.

6. The method of claim 5, wherein the first one of the out-of-plane wrinkles has a maximum amplitude relative to respective amplitudes of corresponding other ones of the out-of-plane wrinkles.

7. The method of claim 1, wherein the B-scan ultrasound image is a first one of a plurality of B-scan ultrasound images generated in response to the scanning of the first side of the composite laminate, and wherein the out-of-plane wrinkle has a maximum amplitude on the first one of the B-scan ultrasound images relative to respective amplitudes of a same out-of-plane wrinkle on other ones of the B-scan ultrasound images.

8. The method of claim 1, further comprising:
generating a C-scan ultrasound image based on ultrasonic C-scan data obtained via the ultrasonic transducer in response to the scanning of the first side;
correlating the C-scan ultrasound image with the B-scan ultrasound image;
locating the out-of-plane wrinkle of the composite laminate on the C-scan ultrasound image based on the correlation between the C-scan ultrasound image and the B-scan ultrasound image; and
marking the out-of-plane wrinkle on the first side of the composite laminate based on the location of the out-of-plane wrinkle on the B-scan ultrasound image and on the C-scan ultrasound image.

9. The method of claim 1, wherein the composite laminate is a stringer for an aircraft.

10. A method for non-destructively determining first and second amplitudes of an out-of-plane wrinkle of a composite laminate, the out-of-plane wrinkle located within the composite laminate between a first side of the composite laminate and a second side of the composite laminate, the second side located opposite the first side, the method comprising:
scanning the first side of the composite laminate with a first ultrasonic transducer;
generating a first B-scan ultrasound image based on ultrasonic B-scan data obtained via the first ultrasonic transducer in response to the scanning of the first side;
locating the out-of-plane wrinkle of the composite laminate on the first B-scan ultrasound image;
associating a first marker with the first B-scan ultrasound image, the first marker being a crest line marker located along a crest of the out-of-plane wrinkle on the first B-scan ultrasound image;
associating a second marker with the first B-scan ultrasound image, the second marker being a first center line marker located along a trough focal point of the out-of-plane wrinkle on the first B-scan ultrasound image;
determining the first amplitude of the out-of-plane wrinkle based on a distance between the first marker and the second marker;
scanning the second side of the composite laminate with a second ultrasonic transducer;
generating a second B-scan ultrasound image based on ultrasonic B-scan data obtained via the second ultrasonic transducer in response to the scanning of the second side;
locating the out-of-plane wrinkle of the composite laminate on the second B-scan ultrasound image;
associating a third marker with the second B-scan ultrasound image, the third marker being a trough line marker located along a trough of the out-of-plane wrinkle on the second B-scan ultrasound image;
associating a fourth marker with the second B-scan ultrasound image, the fourth marker being a second center line marker located along a crest focal point of the out-of-plane wrinkle on the second B-scan ultrasound image; and
determining the second amplitude of the out-of-plane wrinkle based on a distance between the third marker and the fourth marker.

11. The method of claim 10, further comprising determining a height of the out-of-plane wrinkle by summing the first amplitude of the out-of-plane wrinkle and the second amplitude of the out-of-plane wrinkle.

12. The method of claim 10, wherein the associating of the first marker with the first B-scan ultrasound image includes electronically applying the first marker to or over the first B-scan ultrasound image, the associating of the second marker with the first B-scan ultrasound image includes electronically applying the second marker to or over the first B-scan ultrasound image, the associating of the third marker with the second B-scan ultrasound image includes electronically applying the third marker to or over the second B-scan ultrasound image, and the associating of the fourth marker with the second B-scan ultrasound image includes electronically applying the fourth marker to or over the second B-scan ultrasound image.

13. The method of claim 10, wherein the composite laminate is not physically altered in response to any of the scanning of the first side of the composite laminate, the generating of the first B-scan ultrasound image, the locating of the out-of-plane wrinkle of the composite laminate on the first B-scan ultrasound image, the associating of the first marker, the associating of the second marker, the determining of the first amplitude, the scanning of the second side of the composite laminate, the generating of the second B-scan ultrasound image, the locating of the out-of-plane wrinkle of the composite laminate on the second B-scan ultrasound image, the associating of the third marker, the associating of the fourth marker, or the determining of the second amplitude.

14. The method of claim 10, wherein the out-of-plane wrinkle is a first one of a plurality of out-of-plane wrinkles on the first B-scan ultrasound image.

15. The method of claim 14, wherein the first one of the out-of-plane wrinkles has a maximum amplitude relative to respective amplitudes of corresponding other ones of the out-of-plane wrinkles.

16. The method of claim 10, wherein the first B-scan ultrasound image is a first one of a plurality of first B-scan ultrasound images generated in response to the scanning of the first side of the composite laminate, and wherein the out-of-plane wrinkle has a maximum amplitude on the first one of the first B-scan ultrasound images relative to respective amplitudes of a same out-of-plane wrinkle on other ones of the first B-scan ultrasound images.

17. The method of claim 10, further comprising:
generating a first C-scan ultrasound image based on ultrasonic C-scan data obtained via the first ultrasonic transducer in response to the scanning of the first side;
correlating the first C-scan ultrasound image with the first B-scan ultrasound image;
locating the out-of-plane wrinkle of the composite laminate on the first C-scan ultrasound image based on the correlation between the first C-scan ultrasound image and the first B-scan ultrasound image; and
marking the out-of-plane wrinkle on the first side of the composite laminate based on the location of the outof-plane wrinkle on the first B-scan ultrasound image and on the first C-scan ultrasound image.

18. The method of claim 10, wherein the composite laminate is a stringer for an aircraft.

\* \* \* \* \*